US008043573B2

(12) United States Patent
Parker et al.

(10) Patent No.: US 8,043,573 B2
(45) Date of Patent: Oct. 25, 2011

(54) ELECTRO-KINETIC AIR TRANSPORTER WITH MECHANISM FOR EMITTER ELECTRODE TRAVEL PAST CLEANING MEMBER

(75) Inventors: Andrew J. Parker, Novato, CA (US); Charles E. Taylor, Punta Gorda, FL (US); Shek Fai Lau, Foster City, CA (US)

(73) Assignee: Tessera, Inc., San Jose, CA (US)

( * ) Notice: Subject to any disclaimer, the term of this patent is extended or adjusted under 35 U.S.C. 154(b) by 0 days.

(21) Appl. No.: 12/702,232

(22) Filed: Feb. 8, 2010

(65) Prior Publication Data

US 2010/0147150 A1    Jun. 17, 2010

Related U.S. Application Data

(63) Continuation of application No. 11/061,967, filed on Feb. 18, 2005, now abandoned.

(60) Provisional application No. 60/545,698, filed on Feb. 18, 2004.

(51) Int. Cl.
*B01J 19/08* (2006.01)

(52) U.S. Cl. ............ 422/186; 96/29; 96/39; 96/51; 96/94; 96/96; 95/74; 95/75; 95/76; 95/77

(58) Field of Classification Search ........... 422/186; 96/29, 39–42, 51, 94, 96, 97; 95/74–77
See application file for complete search history.

(56) References Cited

U.S. PATENT DOCUMENTS

| | | |
|---|---|---|
| 653,421 A | 7/1900 | Lorey |
| 895,729 A | 8/1908 | Carlborg |
| 995,958 A | 6/1911 | Goldberg |
| 1,791,338 A | 2/1931 | Wintermute |
| 1,869,335 A | 7/1932 | Day |
| 1,882,949 A | 10/1932 | Ruder |
| 2,129,783 A | 9/1938 | Penney |
| 2,327,588 A | 8/1943 | Bennett |

(Continued)

FOREIGN PATENT DOCUMENTS

CN    2111112 U    7/1972

(Continued)

OTHER PUBLICATIONS

U.S. Appl. No. 60/104,573, filed Oct. 16, 1998, Krichtafovitch.

(Continued)

*Primary Examiner* — Jeffrey T Barton
*Assistant Examiner* — Xiuyu Tai
(74) *Attorney, Agent, or Firm* — Zagorin O'Brien Graham LLP

(57) ABSTRACT

Systems and methods for cleaning emitter electrodes of air conditioner systems are provided. The air conditioning system includes an emitter electrode, a collector electrode and a high voltage generator to provide a high voltage potential difference between the emitter and collector electrodes. The system also includes a cleaning member having a channel through which the emitter electrode passes. A plunger mechanism and a spring, or a lever and a fulcrum, are used to force the cleaning member to travel upward along the emitter electrode to thereby frictionally removing debris from the emitter electrode. This description is not intended to be a complete description of, or limit the scope of, the invention. Other features, aspects, and objects of the invention can be obtained from a review of the specification, the figures and the claims.

30 Claims, 11 Drawing Sheets

U.S. PATENT DOCUMENTS

| | | |
|---|---|---|
| 2,359,057 A | 9/1944 | Skinner |
| 2,509,548 A | 5/1950 | White |
| 2,590,447 A | 3/1952 | Nord et al. |
| 2,949,550 A | 8/1960 | Brown |
| 3,018,394 A | 1/1962 | Brown |
| 3,026,964 A | 3/1962 | Penney |
| 3,374,941 A | 3/1968 | Okress |
| 3,518,462 A | 6/1970 | Brown |
| 3,540,191 A | 11/1970 | Herman |
| 3,581,470 A | 6/1971 | Aitkenhead et al. |
| 3,638,058 A | 1/1972 | Fritzius |
| 3,744,216 A | 7/1973 | Halloran |
| 3,806,763 A | 4/1974 | Masuda |
| 3,892,927 A | 7/1975 | Lindenberg |
| 3,945,813 A | 3/1976 | Iinoya et al. |
| 3,958,960 A | 5/1976 | Bakke |
| 3,958,961 A | 5/1976 | Bakke |
| 3,958,962 A | 5/1976 | Hayashi |
| 3,981,695 A | 9/1976 | Fuchs |
| 3,984,215 A | 10/1976 | Zucker |
| 3,988,131 A | 10/1976 | Kanazawa et al. |
| 4,007,024 A | 2/1977 | Sallee et al. |
| 4,052,177 A | 10/1977 | Kide |
| 4,056,372 A | 11/1977 | Hayashi |
| 4,070,163 A | 1/1978 | Kolb et al. |
| 4,074,983 A | 2/1978 | Bakke |
| 4,092,134 A | 5/1978 | Kikuchi |
| 4,097,252 A | 6/1978 | Kirchhoff et al. |
| 4,102,654 A | 7/1978 | Pellin |
| 4,104,042 A | 8/1978 | Brozenick |
| 4,110,086 A | 8/1978 | Schwab et al. |
| 4,119,415 A | 10/1978 | Hayashi et al. |
| 4,126,434 A | 11/1978 | Keiichi |
| 4,138,233 A | 2/1979 | Masuda |
| 4,147,522 A | 4/1979 | Gonas et al. |
| 4,155,792 A | 5/1979 | Gelhaar et al. |
| 4,171,975 A | 10/1979 | Kato et al. |
| 4,185,971 A * | 1/1980 | Isahaya .............................. 96/40 |
| 4,189,308 A | 2/1980 | Feldman |
| 4,205,969 A | 6/1980 | Matsumoto |
| 4,209,306 A | 6/1980 | Feldman et al. |
| 4,218,225 A | 8/1980 | Kirchhoff et al. |
| 4,225,323 A | 9/1980 | Zarchy et al. |
| 4,227,894 A | 10/1980 | Proynoff |
| 4,231,766 A | 11/1980 | Spurgin |
| 4,232,355 A | 11/1980 | Finger et al. |
| 4,244,710 A | 1/1981 | Burger |
| 4,244,712 A | 1/1981 | Tongret |
| 4,251,234 A | 2/1981 | Chang |
| 4,253,852 A | 3/1981 | Adams |
| 4,259,093 A | 3/1981 | Vlastos et al. |
| 4,259,452 A | 3/1981 | Yukuta et al. |
| 4,259,707 A | 3/1981 | Penney |
| 4,264,343 A | 4/1981 | Natarajan et al. |
| 4,266,948 A | 5/1981 | Teague et al. |
| 4,282,014 A | 8/1981 | Winkler et al. |
| 4,284,420 A | 8/1981 | Borysiak |
| 4,289,504 A | 9/1981 | Scholes |
| 4,293,319 A | 10/1981 | Claassen, Jr. |
| 4,308,036 A | 12/1981 | Zahedi et al. |
| 4,315,188 A | 2/1982 | Cerny et al. |
| 4,318,718 A | 3/1982 | Utsumi et al. |
| 4,338,560 A | 7/1982 | Lemley |
| 4,342,571 A | 8/1982 | Hayashi |
| 4,349,359 A | 9/1982 | Fitch et al. |
| 4,351,648 A | 9/1982 | Penney |
| 4,354,861 A | 10/1982 | Kalt |
| 4,357,150 A | 11/1982 | Masuda et al. |
| 4,362,632 A | 12/1982 | Jacob |
| 4,363,072 A | 12/1982 | Coggins |
| 4,366,525 A | 12/1982 | Baumgartner |
| 4,369,776 A | 1/1983 | Roberts |
| 4,375,364 A | 3/1983 | Van Hoesen et al. |
| 4,380,900 A | 4/1983 | Linder et al. |
| 4,386,395 A | 5/1983 | Francis, Jr. |
| 4,391,614 A | 7/1983 | Rozmus |
| 4,394,239 A | 7/1983 | Kitzelmann et al. |
| 4,405,342 A | 9/1983 | Bergman |
| 4,406,671 A | 9/1983 | Rozmus |
| 4,412,850 A | 11/1983 | Kurata et al. |
| 4,413,225 A | 11/1983 | Donig et al. |
| 4,414,603 A | 11/1983 | Masuda |
| 4,435,190 A | 3/1984 | Taillet et al. |
| 4,440,552 A | 4/1984 | Uchiya et al. |
| 4,443,234 A | 4/1984 | Carlsson |
| 4,445,911 A | 5/1984 | Lind |
| 4,477,263 A | 10/1984 | Shaver et al. |
| 4,477,268 A | 10/1984 | Kalt |
| 4,481,017 A | 11/1984 | Furlong |
| 4,496,375 A | 1/1985 | Le Vantine |
| 4,502,002 A | 2/1985 | Ando |
| 4,505,724 A | 3/1985 | Baab |
| 4,509,958 A | 4/1985 | Masuda et al. |
| 4,514,780 A | 4/1985 | Brussee et al. |
| 4,515,982 A | 5/1985 | Lechtken et al. |
| 4,516,991 A | 5/1985 | Kawashima |
| 4,521,229 A | 6/1985 | Baker et al. |
| 4,522,634 A | 6/1985 | Frank |
| 4,534,776 A | 8/1985 | Mammel et al. |
| 4,536,698 A | 8/1985 | Shevalenko et al. |
| 4,544,382 A | 10/1985 | Taillet et al. |
| 4,555,252 A | 11/1985 | Eckstein |
| 4,569,684 A | 2/1986 | Ibbott |
| 4,582,961 A | 4/1986 | Frederiksen |
| 4,587,475 A | 5/1986 | Finney, Jr. et al. |
| 4,588,423 A | 5/1986 | Gillingham et al. |
| 4,590,042 A | 5/1986 | Drage |
| 4,597,780 A | 7/1986 | Reif |
| 4,597,781 A | 7/1986 | Spector |
| 4,600,411 A | 7/1986 | Santamaria |
| 4,601,733 A | 7/1986 | Ordines et al. |
| 4,604,174 A | 8/1986 | Bollinger et al. |
| 4,614,573 A | 9/1986 | Masuda |
| 4,623,365 A | 11/1986 | Bergman |
| 4,626,261 A | 12/1986 | Jorgensen |
| 4,632,135 A | 12/1986 | Lenting et al. |
| 4,632,746 A | 12/1986 | Bergman |
| 4,636,981 A | 1/1987 | Ogura |
| 4,643,744 A | 2/1987 | Brooks |
| 4,643,745 A | 2/1987 | Sakakibara et al. |
| 4,647,836 A | 3/1987 | Olsen |
| 4,650,648 A | 3/1987 | Beer et al. |
| 4,656,010 A | 4/1987 | Leitzke et al. |
| 4,657,738 A | 4/1987 | Kanter et al. |
| 4,659,342 A | 4/1987 | Lind |
| 4,662,903 A | 5/1987 | Yanagawa |
| 4,666,474 A | 5/1987 | Cook |
| 4,668,479 A | 5/1987 | Manabe et al. |
| 4,670,026 A | 6/1987 | Hoenig |
| 4,674,003 A | 6/1987 | Zylka |
| 4,680,496 A | 7/1987 | Letournel et al. |
| 4,686,370 A | 8/1987 | Blach |
| 4,689,056 A | 8/1987 | Noguchi et al. |
| 4,691,829 A | 9/1987 | Auer |
| 4,692,174 A | 9/1987 | Gelfand et al. |
| 4,693,869 A | 9/1987 | Pfaff |
| 4,694,376 A | 9/1987 | Gesslauer |
| 4,702,752 A | 10/1987 | Yanagawa |
| 4,713,092 A | 12/1987 | Kikuchi et al. |
| 4,713,093 A | 12/1987 | Hansson |
| 4,713,724 A | 12/1987 | Voelkel |
| 4,715,870 A | 12/1987 | Masuda et al. |
| 4,725,289 A | 2/1988 | Quintilian |
| 4,726,812 A | 2/1988 | Hirth |
| 4,726,814 A | 2/1988 | Weitman |
| 4,736,127 A | 4/1988 | Jacobsen |
| 4,743,275 A | 5/1988 | Flanagan |
| 4,749,390 A | 6/1988 | Burnett et al. |
| 4,750,921 A | 6/1988 | Sugita et al. |
| 4,760,302 A | 7/1988 | Jacobsen |
| 4,760,303 A | 7/1988 | Miyake |
| 4,765,802 A | 8/1988 | Gombos et al. |
| 4,771,361 A | 9/1988 | Varga |
| 4,772,297 A | 9/1988 | Anzai |
| 4,779,182 A | 10/1988 | Mickal et al. |
| 4,781,736 A | 11/1988 | Cheney et al. |
| 4,786,844 A | 11/1988 | Farrell et al. |

| Patent No. | Date | Name |
|---|---|---|
| 4,789,801 A | 12/1988 | Lee |
| 4,808,200 A | 2/1989 | Dallhammer et al. |
| 4,811,159 A | 3/1989 | Foster, Jr. |
| 4,822,381 A | 4/1989 | Mosley et al. |
| 4,853,005 A | 8/1989 | Jaisinghani et al. |
| 4,869,736 A | 9/1989 | Ivester et al. |
| 4,892,713 A | 1/1990 | Newman |
| 4,929,139 A | 5/1990 | Vorreiter et al. |
| 4,940,470 A | 7/1990 | Jaisinghani et al. |
| 4,940,894 A | 7/1990 | Morters |
| 4,941,068 A | 7/1990 | Hofmann |
| 4,941,224 A | 7/1990 | Saeki et al. |
| 4,944,778 A | 7/1990 | Yanagawa |
| 4,954,320 A | 9/1990 | Birmingham et al. |
| 4,955,991 A | 9/1990 | Torok et al. |
| 4,966,666 A | 10/1990 | Waltonen |
| 4,967,119 A | 10/1990 | Torok et al. |
| 4,976,752 A | 12/1990 | Torok et al. |
| 4,978,372 A | 12/1990 | Pick |
| D315,598 S | 3/1991 | Yamamoto et al. |
| 5,003,774 A | 4/1991 | Leonard |
| 5,006,761 A | 4/1991 | Torok et al. |
| 5,010,869 A | 4/1991 | Lee |
| 5,012,093 A | 4/1991 | Shimizu |
| 5,012,094 A | 4/1991 | Hamade |
| 5,012,159 A | 4/1991 | Torok et al. |
| 5,022,979 A | 6/1991 | Hijikata et al. |
| 5,024,685 A | 6/1991 | Torok et al. |
| 5,030,254 A | 7/1991 | Heyen et al. |
| 5,037,456 A | 8/1991 | Yu |
| 5,045,095 A | 9/1991 | You |
| 5,053,912 A | 10/1991 | Loreth et al. |
| 5,059,219 A | 10/1991 | Plaks et al. |
| 5,061,462 A | 10/1991 | Suzuki |
| 5,066,313 A | 11/1991 | Mallory, Sr. |
| 5,072,746 A | 12/1991 | Kantor |
| 5,076,820 A | 12/1991 | Gurvitz |
| 5,077,468 A | 12/1991 | Hamade |
| 5,077,500 A | 12/1991 | Torok et al. |
| 5,100,440 A | 3/1992 | Stahel et al. |
| RE33,927 E | 5/1992 | Fuzimura |
| D326,514 S | 5/1992 | Alsup et al. |
| 5,118,942 A | 6/1992 | Hamade |
| 5,125,936 A | 6/1992 | Johansson |
| 5,136,461 A | 8/1992 | Zellweger |
| 5,137,546 A | 8/1992 | Steinbacher et al. |
| 5,141,529 A | 8/1992 | Oakley et al. |
| 5,141,715 A | 8/1992 | Sackinger et al. |
| D329,284 S | 9/1992 | Patton |
| 5,147,429 A | 9/1992 | Bartholomew et al. |
| 5,154,733 A | 10/1992 | Fujii et al. |
| 5,158,580 A | 10/1992 | Chang |
| D332,655 S | 1/1993 | Lytle et al. |
| 5,180,404 A | 1/1993 | Loreth et al. |
| 5,183,480 A | 2/1993 | Raterman et al. |
| 5,196,171 A | 3/1993 | Peltier |
| 5,198,003 A | 3/1993 | Haynes |
| 5,199,257 A | 4/1993 | Colletta et al. |
| 5,210,678 A | 5/1993 | Lain et al. |
| 5,215,558 A | 6/1993 | Moon |
| 5,217,504 A | 6/1993 | Johansson |
| 5,217,511 A | 6/1993 | Plaks et al. |
| 5,234,555 A | 8/1993 | Ibbott |
| 5,248,324 A | 9/1993 | Hara |
| 5,250,267 A | 10/1993 | Johnson et al. |
| 5,254,155 A | 10/1993 | Mensi |
| 5,266,004 A | 11/1993 | Tsumurai et al. |
| 5,271,763 A | 12/1993 | Jang |
| 5,282,891 A | 2/1994 | Durham |
| 5,290,343 A | 3/1994 | Morita et al. |
| 5,296,019 A | 3/1994 | Oakley et al. |
| 5,302,190 A | 4/1994 | Williams |
| 5,308,586 A | 5/1994 | Fritsche et al. |
| 5,315,838 A | 5/1994 | Thompson |
| 5,316,741 A | 5/1994 | Sewell et al. |
| 5,330,559 A | 7/1994 | Cheney et al. |
| 5,348,571 A | 9/1994 | Weber |
| 5,376,168 A | 12/1994 | Inculet |
| 5,378,978 A | 1/1995 | Gallo et al. |
| 5,386,839 A | 2/1995 | Chen |
| 5,395,430 A | 3/1995 | Lundgren et al. |
| 5,401,301 A | 3/1995 | Schulmerich et al. |
| 5,401,302 A | 3/1995 | Schulmerich et al. |
| 5,403,383 A | 4/1995 | Jaisinghani |
| 5,405,434 A | 4/1995 | Inculet |
| 5,407,469 A | 4/1995 | Sun |
| 5,407,639 A | 4/1995 | Watanabe et al. |
| 5,417,936 A | 5/1995 | Suzuki et al. |
| 5,419,953 A | 5/1995 | Chapman |
| 5,433,772 A | 7/1995 | Sikora |
| 5,435,817 A | 7/1995 | Davis et al. |
| 5,435,978 A | 7/1995 | Yokomi |
| 5,437,713 A | 8/1995 | Chang |
| 5,437,843 A | 8/1995 | Kuan |
| 5,445,798 A | 8/1995 | Ikeda et al. |
| 5,466,279 A | 11/1995 | Hattori et al. |
| 5,468,454 A | 11/1995 | Kim |
| 5,474,599 A | 12/1995 | Cheney et al. |
| 5,484,472 A | 1/1996 | Weinberg |
| 5,484,473 A | 1/1996 | Bontempi |
| 5,492,678 A | 2/1996 | Ota et al. |
| 5,501,844 A | 3/1996 | Kasting, Jr. et al. |
| 5,503,808 A | 4/1996 | Garbutt et al. |
| 5,503,809 A | 4/1996 | Coate et al. |
| 5,505,914 A | 4/1996 | Tona-Serra |
| 5,508,008 A | 4/1996 | Wasser |
| 5,514,345 A | 5/1996 | Garbutt et al. |
| 5,516,493 A | 5/1996 | Bell et al. |
| 5,518,531 A | 5/1996 | Joannu |
| 5,520,887 A | 5/1996 | Shimizu et al. |
| 5,525,310 A | 6/1996 | Decker et al. |
| 5,529,613 A | 6/1996 | Yavnieli |
| 5,529,760 A | 6/1996 | Burris |
| 5,532,798 A | 7/1996 | Nakagami et al. |
| 5,535,089 A | 7/1996 | Ford et al. |
| 5,536,477 A | 7/1996 | Cha et al. |
| 5,538,695 A | 7/1996 | Shinjo et al. |
| 5,540,761 A | 7/1996 | Yamamoto |
| 5,542,967 A | 8/1996 | Ponizovsky et al. |
| 5,545,379 A | 8/1996 | Gray |
| 5,545,380 A | 8/1996 | Gray |
| 5,547,643 A | 8/1996 | Nomoto et al. |
| 5,549,874 A | 8/1996 | Kamiya et al. |
| 5,554,344 A | 9/1996 | Duarte |
| 5,554,345 A | 9/1996 | Kitchenman |
| 5,569,368 A | 10/1996 | Larsky et al. |
| 5,569,437 A | 10/1996 | Stiehl et al. |
| D375,546 S | 11/1996 | Lee |
| 5,571,483 A | 11/1996 | Pfingstl et al. |
| 5,573,577 A | 11/1996 | Joannou |
| 5,573,730 A | 11/1996 | Gillum |
| 5,578,112 A | 11/1996 | Krause |
| 5,578,280 A | 11/1996 | Kazi et al. |
| 5,582,632 A | 12/1996 | Nohr et al. |
| 5,587,131 A | 12/1996 | Malkin et al. |
| D377,523 S | 1/1997 | Marvin et al. |
| 5,591,253 A | 1/1997 | Altman et al. |
| 5,591,334 A | 1/1997 | Shimizu et al. |
| 5,591,412 A | 1/1997 | Jones et al. |
| 5,593,476 A | 1/1997 | Coppom |
| 5,601,636 A | 2/1997 | Glucksman |
| 5,603,752 A | 2/1997 | Hara |
| 5,603,893 A | 2/1997 | Gundersen et al. |
| 5,614,002 A | 3/1997 | Chen |
| 5,624,476 A | 4/1997 | Eyraud |
| 5,630,866 A | 5/1997 | Gregg |
| 5,630,990 A | 5/1997 | Conrad et al. |
| 5,637,198 A | 6/1997 | Breault |
| 5,637,279 A | 6/1997 | Besen et al. |
| 5,641,342 A | 6/1997 | Smith et al. |
| 5,641,461 A | 6/1997 | Ferone |
| 5,647,890 A | 7/1997 | Yamamoto |
| 5,648,049 A | 7/1997 | Jones et al. |
| 5,655,210 A | 8/1997 | Gregoire et al. |
| 5,656,063 A | 8/1997 | Hsu |
| 5,665,147 A | 9/1997 | Taylor et al. |
| 5,667,563 A | 9/1997 | Silva, Jr. |
| 5,667,564 A | 9/1997 | Weinberg |

| | | |
|---|---|---|
| 5,667,565 A | 9/1997 | Gondar |
| 5,667,756 A | 9/1997 | Ho |
| 5,669,963 A | 9/1997 | Horton et al. |
| 5,678,237 A | 10/1997 | Powell et al. |
| 5,681,434 A | 10/1997 | Eastlund |
| 5,681,533 A | 10/1997 | Hiromi |
| 5,698,164 A | 12/1997 | Kishioka et al. |
| 5,702,507 A | 12/1997 | Wang |
| D389,567 S | 1/1998 | Gudefin |
| 5,766,318 A | 6/1998 | Loreth et al. |
| 5,779,769 A | 7/1998 | Jiang |
| 5,814,135 A | 9/1998 | Weinberg |
| 5,879,435 A | 3/1999 | Satyapal et al. |
| 5,893,977 A | 4/1999 | Pucci |
| 5,911,957 A | 6/1999 | Khatchatrian et al. |
| 5,972,076 A | 10/1999 | Nichols et al. |
| 5,975,090 A | 11/1999 | Taylor et al. |
| 5,980,614 A | 11/1999 | Loreth et al. |
| 5,993,521 A | 11/1999 | Loreth et al. |
| 5,997,619 A | 12/1999 | Knuth et al. |
| 6,019,815 A | 2/2000 | Satyapal et al. |
| 6,042,637 A | 3/2000 | Weinberg |
| 6,063,168 A | 5/2000 | Nichols et al. |
| 6,086,657 A | 7/2000 | Freije |
| 6,117,216 A | 9/2000 | Loreth |
| 6,118,645 A | 9/2000 | Partridge |
| 6,126,722 A | 10/2000 | Mitchell et al. |
| 6,126,727 A | 10/2000 | Lo |
| 6,149,717 A | 11/2000 | Satyapal et al. |
| 6,149,815 A | 11/2000 | Sauter |
| 6,152,146 A | 11/2000 | Taylor et al. |
| 6,163,098 A | 12/2000 | Taylor et al. |
| 6,176,977 B1 | 1/2001 | Taylor et al. |
| 6,182,461 B1 | 2/2001 | Washburn et al. |
| 6,182,671 B1 | 2/2001 | Taylor et al. |
| 6,193,852 B1 | 2/2001 | Caracciolo et al. |
| 6,203,600 B1 | 3/2001 | Loreth |
| 6,212,883 B1 | 4/2001 | Kang |
| 6,228,149 B1 | 5/2001 | Alenichev et al. |
| 6,252,012 B1 | 6/2001 | Egitto et al. |
| 6,270,733 B1 | 8/2001 | Rodden |
| 6,277,248 B1 | 8/2001 | Ishioka et al. |
| 6,282,106 B2 | 8/2001 | Grass |
| D449,097 S | 10/2001 | Smith et al. |
| D449,679 S | 10/2001 | Smith et al. |
| 6,296,692 B1 | 10/2001 | Gutmann |
| 6,302,944 B1 | 10/2001 | Hoenig |
| 6,309,514 B1 | 10/2001 | Conrad et al. |
| 6,312,507 B1 | 11/2001 | Taylor et al. |
| 6,315,821 B1 | 11/2001 | Pillion et al. |
| 6,328,791 B1 | 12/2001 | Pillion et al. |
| 6,348,103 B1 | 2/2002 | Ahlborn et al. |
| 6,350,417 B1 | 2/2002 | Lau et al. |
| 6,362,604 B1 | 3/2002 | Cravey |
| 6,372,097 B1 | 4/2002 | Chen |
| 6,373,723 B1 | 4/2002 | Wallgren et al. |
| 6,379,427 B1 | 4/2002 | Siess |
| 6,391,259 B1 | 5/2002 | Malkin et al. |
| 6,398,852 B1 | 6/2002 | Loreth |
| 6,447,587 B1 | 9/2002 | Pillion et al. |
| 6,451,266 B1 | 9/2002 | Lau et al. |
| 6,464,754 B1 | 10/2002 | Ford |
| 6,471,753 B1 | 10/2002 | Ahn et al. |
| 6,494,940 B1 | 12/2002 | Hak |
| 6,504,308 B1 | 1/2003 | Krichtafovitch et al. |
| 6,508,982 B1 | 1/2003 | Shoji |
| 6,544,485 B1 | 4/2003 | Taylor |
| 6,558,456 B2 * | 5/2003 | Nissinen ............. 96/39 |
| 6,585,935 B1 | 7/2003 | Taylor et al. |
| 6,588,434 B2 | 7/2003 | Taylor et al. |
| 6,603,268 B2 | 8/2003 | Lee |
| 6,613,277 B1 | 9/2003 | Monagan |
| 6,632,407 B1 | 10/2003 | Lau et al. |
| 6,635,105 B2 | 10/2003 | Ahlborn et al. |
| 6,672,315 B2 | 1/2004 | Taylor et al. |
| 6,709,484 B2 | 3/2004 | Lau et al. |
| 6,713,026 B2 | 3/2004 | Taylor et al. |
| 6,735,830 B1 | 5/2004 | Merciel |
| 6,749,667 B2 | 6/2004 | Reeves et al. |
| 6,753,652 B2 | 6/2004 | Kim |
| 6,761,796 B2 | 7/2004 | Srivastava et al. |
| 6,768,108 B2 | 7/2004 | Hirano et al. |
| 6,768,110 B2 | 7/2004 | Alani |
| 6,768,120 B2 | 7/2004 | Leung et al. |
| 6,768,121 B2 | 7/2004 | Horsky |
| 6,770,878 B2 | 8/2004 | Uhlemann et al. |
| 6,774,359 B1 | 8/2004 | Hirabayashi et al. |
| 6,777,686 B2 | 8/2004 | Olson et al. |
| 6,777,699 B1 | 8/2004 | Miley et al. |
| 6,777,882 B2 | 8/2004 | Goldberg et al. |
| 6,781,136 B1 | 8/2004 | Kato |
| 6,785,912 B1 | 9/2004 | Julio |
| 6,791,814 B2 | 9/2004 | Adachi et al. |
| 6,794,661 B2 | 9/2004 | Tsukihara et al. |
| 6,797,339 B2 | 9/2004 | Akizuki et al. |
| 6,797,964 B2 | 9/2004 | Yamashita |
| 6,799,068 B1 | 9/2004 | Hartmann et al. |
| 6,800,862 B2 | 10/2004 | Matsumoto et al. |
| 6,803,585 B2 | 10/2004 | Glukhoy |
| 6,805,916 B2 | 10/2004 | Cadieu |
| 6,806,035 B1 | 10/2004 | Atireklapvarodom et al. |
| 6,806,163 B2 | 10/2004 | Wu et al. |
| 6,806,468 B2 | 10/2004 | Laiko et al. |
| 6,808,606 B2 | 10/2004 | Thomsen et al. |
| 6,809,310 B2 | 10/2004 | Chen |
| 6,809,312 B1 | 10/2004 | Park et al. |
| 6,809,325 B2 | 10/2004 | Dahl et al. |
| 6,812,647 B2 | 11/2004 | Cornelius |
| 6,815,690 B2 | 11/2004 | Veerasamy et al. |
| 6,818,257 B2 | 11/2004 | Amann et al. |
| 6,818,909 B2 | 11/2004 | Murrell et al. |
| 6,819,053 B2 | 11/2004 | Johnson |
| 6,863,869 B2 | 3/2005 | Lau et al. |
| 6,896,853 B2 | 5/2005 | Lau et al. |
| 6,911,186 B2 | 6/2005 | Taylor et al. |
| 2001/0048906 A1 | 12/2001 | Lau et al. |
| 2002/0069760 A1 | 6/2002 | Pruette et al. |
| 2002/0079212 A1 | 6/2002 | Taylor et al. |
| 2002/0098131 A1 | 7/2002 | Taylor et al. |
| 2002/0122751 A1 | 9/2002 | Sinaiko et al. |
| 2002/0122752 A1 | 9/2002 | Taylor et al. |
| 2002/0127156 A1 | 9/2002 | Taylor |
| 2002/0134664 A1 | 9/2002 | Taylor et al. |
| 2002/0134665 A1 | 9/2002 | Taylor et al. |
| 2002/0141914 A1 | 10/2002 | Lau et al. |
| 2002/0144601 A1 | 10/2002 | Palestro et al. |
| 2002/0146356 A1 | 10/2002 | Sinaiko et al. |
| 2002/0150520 A1 | 10/2002 | Taylor et al. |
| 2002/0152890 A1 | 10/2002 | Leiser |
| 2002/0155041 A1 | 10/2002 | McKinney, Jr. et al. |
| 2002/0170435 A1 | 11/2002 | Joannou |
| 2002/0190658 A1 | 12/2002 | Lee |
| 2002/0195951 A1 | 12/2002 | Lee |
| 2003/0005824 A1 | 1/2003 | Katou et al. |
| 2003/0170150 A1 | 9/2003 | Law et al. |
| 2003/0206837 A1 | 11/2003 | Taylor et al. |
| 2003/0206839 A1 | 11/2003 | Taylor et al. |
| 2003/0206840 A1 | 11/2003 | Taylor et al. |
| 2004/0033176 A1 | 2/2004 | Lee et al. |
| 2004/0052700 A1 | 3/2004 | Kotlyar et al. |
| 2004/0065202 A1 | 4/2004 | Gatchell et al. |
| 2004/0096376 A1 | 5/2004 | Taylor |
| 2004/0136863 A1 | 7/2004 | Yates et al. |
| 2004/0166037 A1 | 8/2004 | Youdell et al. |
| 2004/0226447 A1 | 11/2004 | Lau et al. |
| 2004/0234431 A1 | 11/2004 | Taylor et al. |
| 2004/0237787 A1 | 12/2004 | Reeves et al. |
| 2004/0251124 A1 | 12/2004 | Lau |
| 2004/0251909 A1 | 12/2004 | Taylor et al. |
| 2005/0000793 A1 | 1/2005 | Taylor et al. |

FOREIGN PATENT DOCUMENTS

| | | |
|---|---|---|
| CN | 87210843 U | 7/1988 |
| CN | 2138764 Y | 6/1993 |
| CN | 2153231 Y | 12/1993 |
| DE | 2206057 | 8/1973 |
| DE | 3832879 * | 4/1989 |
| DE | 19741621 C1 | 6/1999 |

| | | | |
|---|---|---|---|
| EP | 0433152 | A1 | 12/1990 |
| EP | 0332624 | B1 | 1/1992 |
| FR | 2690509 | | 10/1993 |
| GB | 643363 | | 9/1950 |
| JP | S51-90077 | | 8/1976 |
| JP | S62-20653 | | 2/1987 |
| JP | S63164948 | | 10/1988 |
| JP | 10137007 | | 5/1998 |
| JP | 11104223 | | 4/1999 |
| JP | 2000236914 | | 9/2000 |
| WO | WO92/05875 | A1 | 4/1992 |
| WO | WO96/04703 | A1 | 2/1996 |
| WO | WO99/07474 | A1 | 2/1999 |
| WO | WO00/10713 | A1 | 3/2000 |
| WO | WO01/47803 | A1 | 7/2001 |
| WO | WO01/48781 | A1 | 7/2001 |
| WO | WO01/64349 | A1 | 9/2001 |
| WO | WO01/85348 | A2 | 11/2001 |
| WO | WO02/20162 | A2 | 3/2002 |
| WO | WO02/20163 | A2 | 3/2002 |
| WO | WO02/30574 | A1 | 4/2002 |
| WO | WO02/32578 | A1 | 4/2002 |
| WO | WO02/42003 | A1 | 5/2002 |
| WO | WO02/066167 | A1 | 8/2002 |
| WO | WO03/009944 | A1 | 2/2003 |
| WO | WO03/013620 | A1 | 2/2003 |
| WO | WO03/013734 | A1 | 2/2003 |

OTHER PUBLICATIONS

U.S. Appl. No. 60/306,479, filed Jul. 8, 2001, Taylor.
U.S. Appl. No. 60/340,090, filed Dec. 13, 2001, Taylor.
U.S. Appl. No. 60/340,288, filed Dec. 13, 2001, Taylor.
U.S. Appl. No. 60/340,462, filed Dec. 13, 2001, Taylor.
U.S. Appl. No. 60/340,702, filed Dec. 13, 2001, Taylor et al.
U.S. Appl. No. 60/341,176, filed Dec. 13, 2001, Taylor.
U.S. Appl. No. 60/341,179, filed Dec. 13, 2001, Taylor et al.
U.S. Appl. No. 60/341,320, filed Dec. 13, 2001, Taylor.
U.S. Appl. No. 60/341,377, filed Dec. 13, 2001, Taylor et al.
U.S. Appl. No. 60/341,433, filed Dec. 13, 2001, Taylor.
U.S. Appl. No. 60/341,518, filed Dec. 13, 2001, Taylor.
U.S. Appl. No. 60/341,592, filed Dec. 13, 2001, Taylor.
U.S. Appl. No. 60/391,070, filed Jun. 6, 2002, Reeves.
"Household Air Cleaners," Consumer Reports Magazine—Oct. 1992, 6 pp.
Blueair AV 402 Air Purifier, http://www.air-purifiers-usa.biz/Blueair_AV402.htrn, 4 pp., 1996.
Blueair AV 501 Air Purifier, http://www.air-purifiers-usa.biz/Blueair AV501.htm, 15 pp., 1997.
ConsumerReports org, "Air Cleaners Behind the Hype" http://www.consumerreports.org/main/content/printable.jsp?FOLDER%3C%3EFOLDER_id, Oct. 2003, 6 pp.
Electrical schematic and promotional material available from Zenion Industries, 7 pages, Aug. 1990.
English Translation of German Patent Document DE 19741621 C1; Publication Date: Jun. 10, 1999.
English Translation of German Published Patent Application 2206057; Publication Date: Aug. 16, 1973.
English Translation of Japanese Unexamined Patent Application Bulletin No. S51-90077; Publication Date: Aug. 6, 1976.
English Translation of Japanese Unexamined Utility Model Application No. S62-20653; Publication Date: Feb. 7, 1987.
English Translation of Japanese Unexamined Utility Model Application No. S63-164948; Publication Date: Oct. 27, 1988.
Friedrich C-90A Electronic Air Cleaner, Service Information, Friedrich Air Conditioning Co., 12 pp., 1985.
LakeAir Excel and Maxum Portable Electronic Air Cleaners, Operating and Service Manual, LakeAir International, Inc., 11 pp., 1971.
LENTEK Sila™ Plug-In Air Purifier/Deodorizer product box copyrighted 1999, 13 pages.
Promotional material available from Zenion Industries for the Plasma-Pure 100/200/300, 2 pages, Aug. 1990.
Promotional material available from Zenion Industries for the Plasma-Tron, 2 pages, Aug. 1990.
Trion 120 Air Purifier, Model 442501-025, http://www.feddersoutled.com/trion120.html, 16 pp., believed to be at least one year prior to Nov. 5, 1998.
Trion 150 Air Purifier, Model 45000-002, http://www.feddersoutlet.com/trion150.html, 11 pp., believed to be at least one year prior to Nov. 5, 1998.
Trion 350 Air Purifier, Model 450111-010, http://www.feddersoutlet.com/trion350.html, 12 pp., believed to be at least one year prior to Nov. 5, 1998.
Trion Console 250 Electronic Air Cleaner, Model Series 442857 and 445600, Manual for Installation•Operation•Maintenance, Trion Inc., 7 pp., believed to be at least one year prior to Nov. 5, 1998.

* cited by examiner

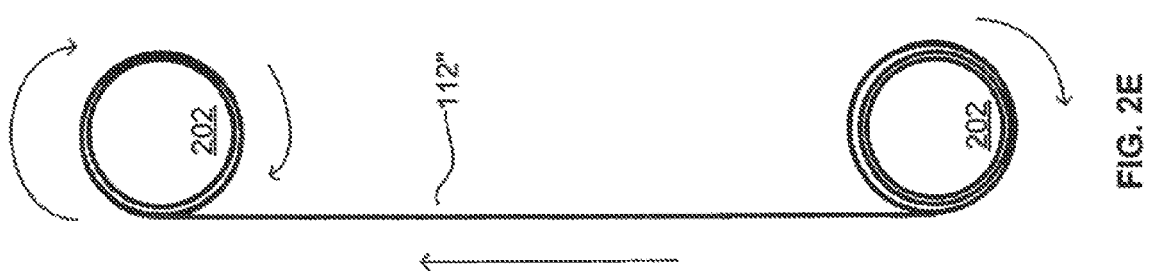

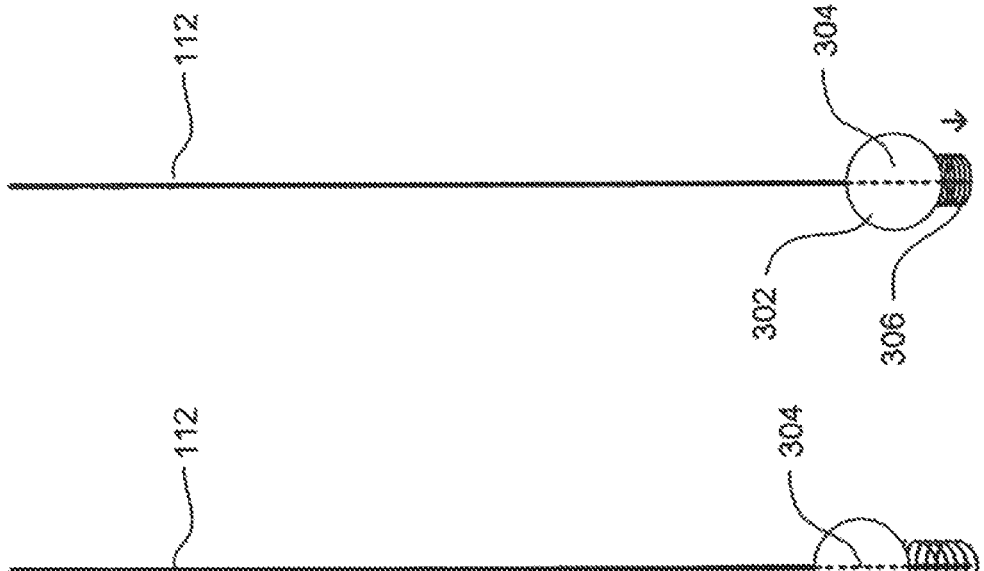

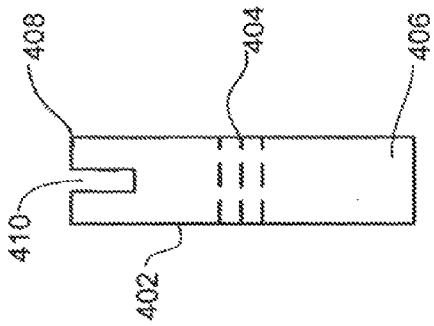
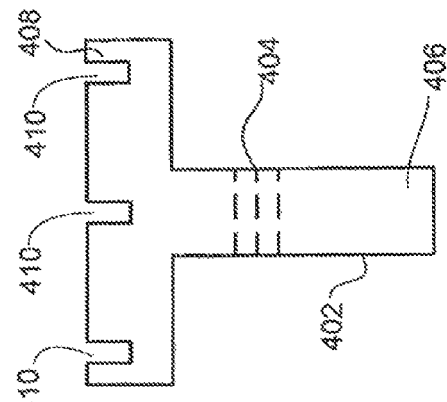
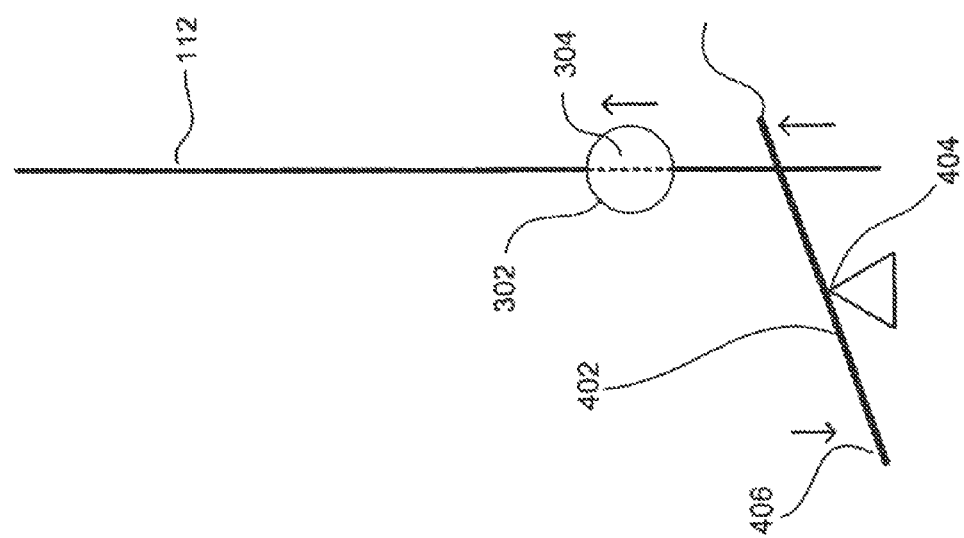
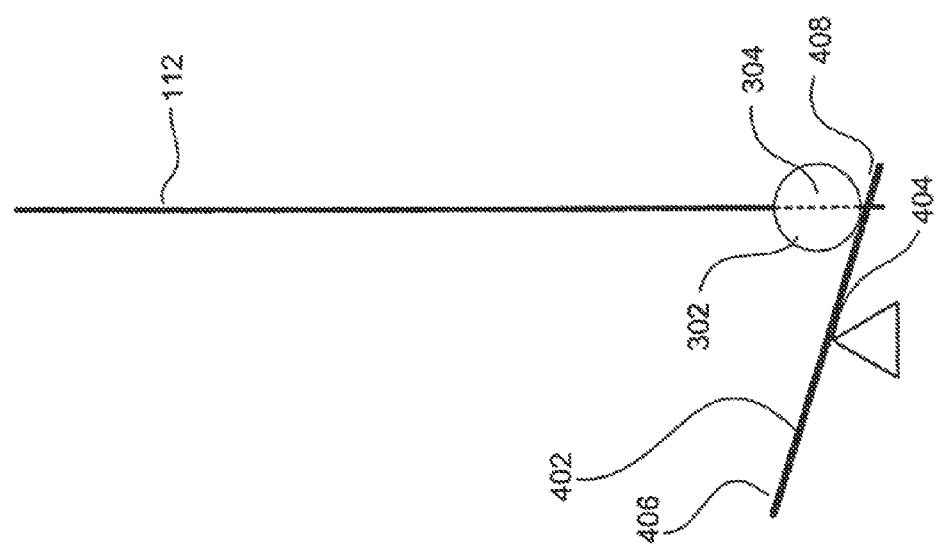

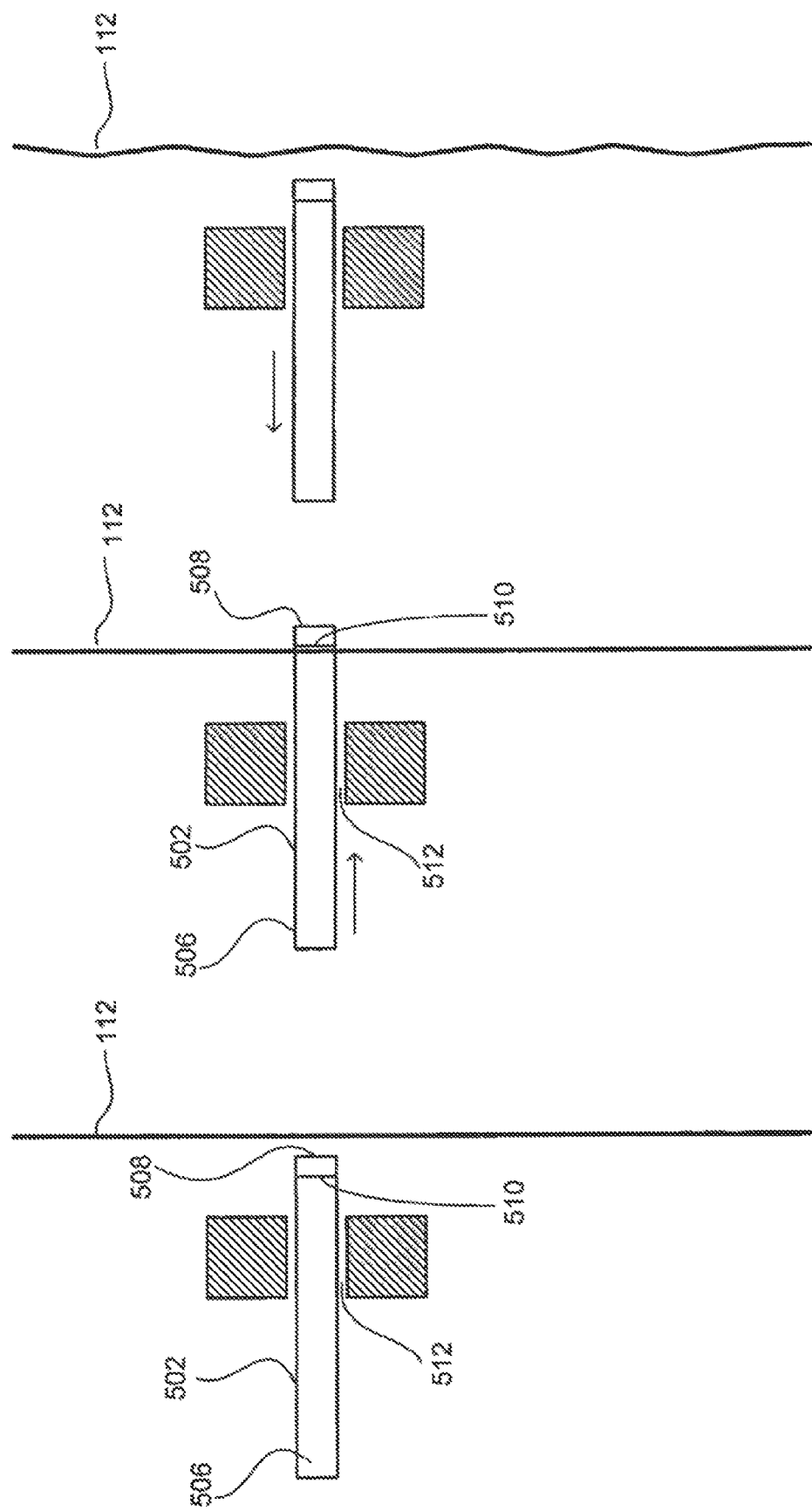

ELECTRO-KINETIC AIR TRANSPORTER WITH MECHANISM FOR EMITTER ELECTRODE TRAVEL PAST CLEANING MEMBER

PRIORITY CLAIM

This application is a continuation of application Ser. No. 11/061,967, filed Feb. 18, 2005, now abandoned by Andrew J. Parker, et al., which claims priority to U.S. Provisional Patent Application No. 60/545,698, filed Feb. 18, 2004, both of which are incorporated herein in their entirety by reference.

FIELD OF THE INVENTION

The present invention relates generally to devices that electrically transport and/or condition air. More specifically, the present invention relates to systems and methods for cleaning the emitter electrodes of such devices.

BACKGROUND OF THE INVENTION

It is known in the art to produce an airflow using electro-kinetic techniques, by which electrical power is converted into a flow of air without mechanically moving components. Such systems were described, for example, in U.S. Pat. No. 4,789,801 to Lee (1988), as well as in U.S. Pat. No. 6,176,977 to Taylor et al. (2001). As is described in these patents, an electro-kinetic air transporter and conditioner system typically includes a first array of emitter electrodes and second array of collector electrodes, with each array including one or more electrodes. Driver electrodes (also known as interstitial electrodes) may also be used, to increase the collecting efficiency of a system. While the collector electrodes are typically in need of cleaning more often then the emitter electrodes, the emitter electrodes can eventually accumulate a deposited layer or coating of fine ash-like material. It would be useful to provide new schemes for cleaning emitter electrodes.

BRIEF DESCRIPTION OF THE FIGURES

FIGS. 2A-2D illustrate various mechanisms for removing debris from the wire loop emitter electrodes of FIG. 2A, in accordance with embodiments of the present invention.

FIG. 2E illustrates an embodiment of the present invention in which a wire emitter electrode is unwound from one spool and wound onto another spool, according to an embodiment of the present invention.

FIGS. 3A-3E illustrate embodiments of the present invention where a spring is used to move, and more specifically project, a cleaning member along an emitter electrode.

FIGS. 4A and 4B illustrate embodiments of the present invention where a lever mechanism is used to move, and more specifically project, a cleaning member along an emitter electrode. FIGS. 4C and 4D are top views of exemplary levers that can be used in the embodiments shown in FIGS. 4A and 4B.

FIGS. 5A-5C illustrate embodiments of the present invention where a plucker is used to vibrate an emitter electrode.

DETAILED DESCRIPTION

Figure 1A:
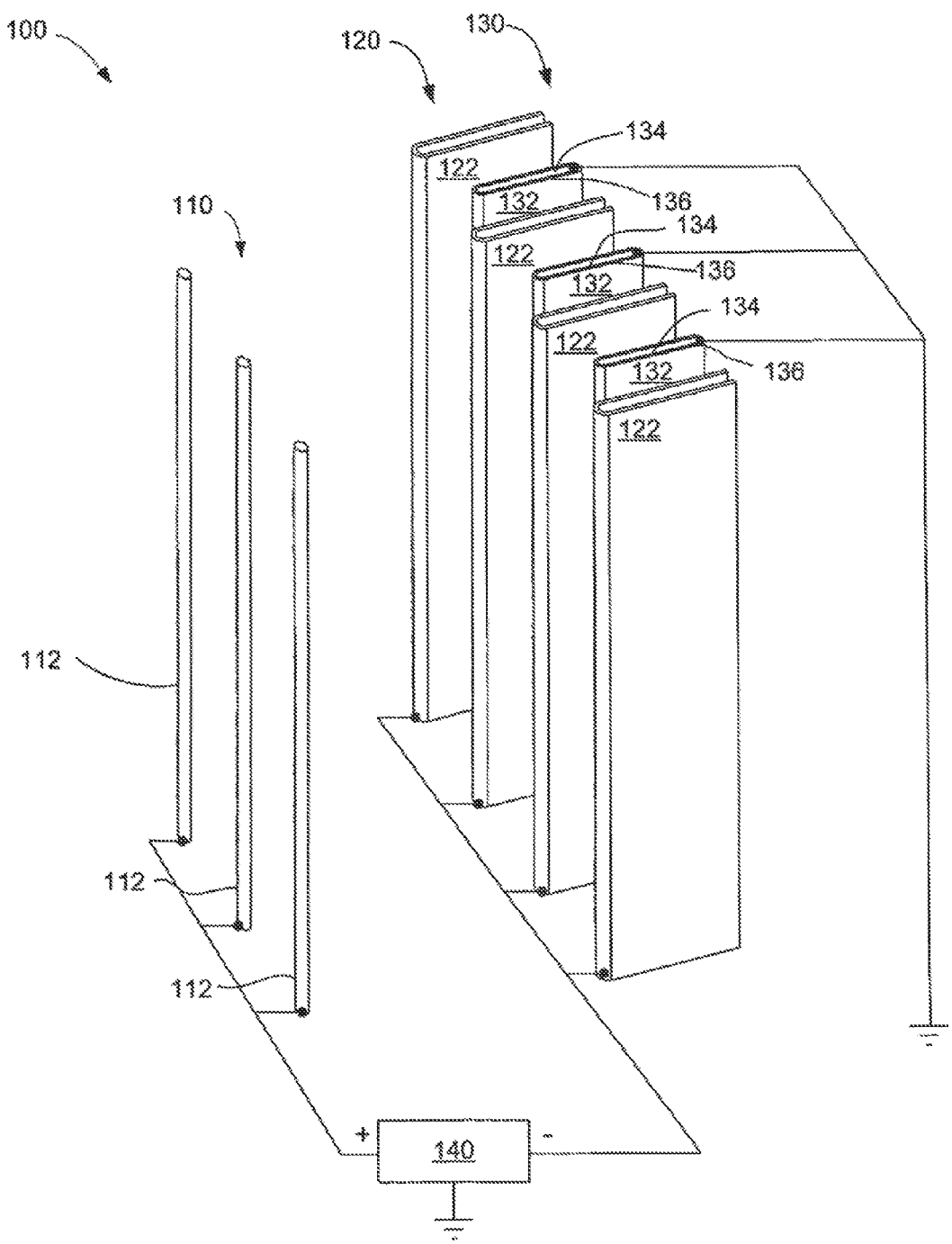
FIGS. 1A and 1B illustrate an exemplary electro-kinetic conditioner system.

The purpose of emitter electrodes (e.g., wire shaped electrodes), of electro-kinetic air transporter and conditioner systems, is to produce a corona discharge that ionizes (i.e., chargers) the particles in the air in the vicinity of the emitter electrodes. Collector electrodes, which typically have an opposite charge as the emitter electrodes, will attract the charged particles, causing the charged particles to stick or collect on the collector electrodes, thereby cleaning the air. As described in U.S. Pat. No. 6,350,417, to Lau et al. (2002) the collector electrodes can be removed from a housing (containing the electrodes), manually cleaned, and then returned to the housing (e.g., through a top of the housing). While the collector electrodes are typically in need of cleaning more often then the emitter electrodes, the emitter electrodes can eventually accumulate a deposited layer or coating of fine ash-like material. Additionally, dendrites may grow on the emitter electrodes. If such deposits (also referred to hereafter as debris) are allowed to accumulate, the efficiency of the system will eventually be degraded. Further, such deposits (i.e., debris) may also produce an audible oscillation that can be annoying to persons near the system.

Accordingly, the '417 patent teaches various schemes for cleaning the emitter electrodes. In one embodiment, a sheet or strip of electrically insulating material extends from a base associated with the collector electrodes. When the collector electrodes are vertically removed from a top of the housing (and when returned to the housing), the insulating material scrapes against the emitter electrodes, frictionally cleaning the emitter electrodes. Additional details are provided in the '417 patent, which is incorporated herein by reference. While this embodiment of the '417 patent is very effective, it would be beneficial to provide further techniques for cleaning emitter electrodes that do not rely on the removal of the collector electrodes.

In another embodiment, the '417 patent teaches the use of bead-like mechanisms to clean emitter electrodes. In this embodiment, the beads have a channel through which the wire-like emitter electrodes extend. By rotating the housing (which contains the electrodes), the beads are caused to slide along the emitter electrodes, thereby frictionally cleaning the emitter electrodes. While this embodiment of the '417 patent is very effective, it would be beneficial to provide further techniques for cleaning emitter electrodes that do not rely on rotation of a housing.

U.S. patent application Ser. No. 10/278,193 to Reeves et al. (now allowed), filed Oct. 21, 2002, discloses a bead lifting mechanism, that causes bead-like cleaners, similar to those in the '417 patent, to be lifted when the collector electrodes are vertically removed from the housing (which contains the electrodes). While this embodiment of the '193 application is very effective, it would be beneficial to provide further techniques for cleaning emitter electrodes that do not rely on removal of the collector electrodes.

Embodiments of the present invention are related to electro-kinetic air transporter-conditioner systems and methods. In accordance with embodiments of the present invention an emitter electrode comprises a wire loop, and debris is frictionally removed from the emitter electrode by a scraper, brush, or cleaning wheel as the wire loop is rotated. In other embodiments, various schemes are provided for causing a cleaning member to move along an emitter electrode, thereby frictionally removing debris from the emitter electrode. In further embodiments, debris is vibrated off an emitter electrode. In still other embodiments, an emitter electrode is heated such that debris is burned off the electrode. Other features and advantages of the invention will appear from the following description in which the preferred embodiments have been set forth in detail, in conjunction with the accompanying drawings and claims.

FIG. 1A illustrates schematically, an exemplary electro-kinetic conditioner system 100. The system includes a first array 110 (i.e., emitter array) of emitter electrodes 112, a second array 120 (i.e., collector array) of collector electrodes 122 and a third array 130 of driver electrodes 130. While each array is shown as including multiple electrodes, an array can include as few as one electrode. In this embodiment, the emitter array 110 is shown as being connected to a positive terminal of a high voltage generator 140, and the collector array 120 is shown as being connected to a negative terminal of the high voltage generator 140. The third array 130 of driver electrodes 132 is shown as being grounded. Each driver electrode can be insulated, as disclosed in U.S. patent application Ser. No. 10/717,420, filed Nov. 19, 2003, which is incorporated herein by reference. Further, it is noted that embodiments of the present invention also relate to electrode arrangements that do not include driver electrodes 132.

Figure 1B:
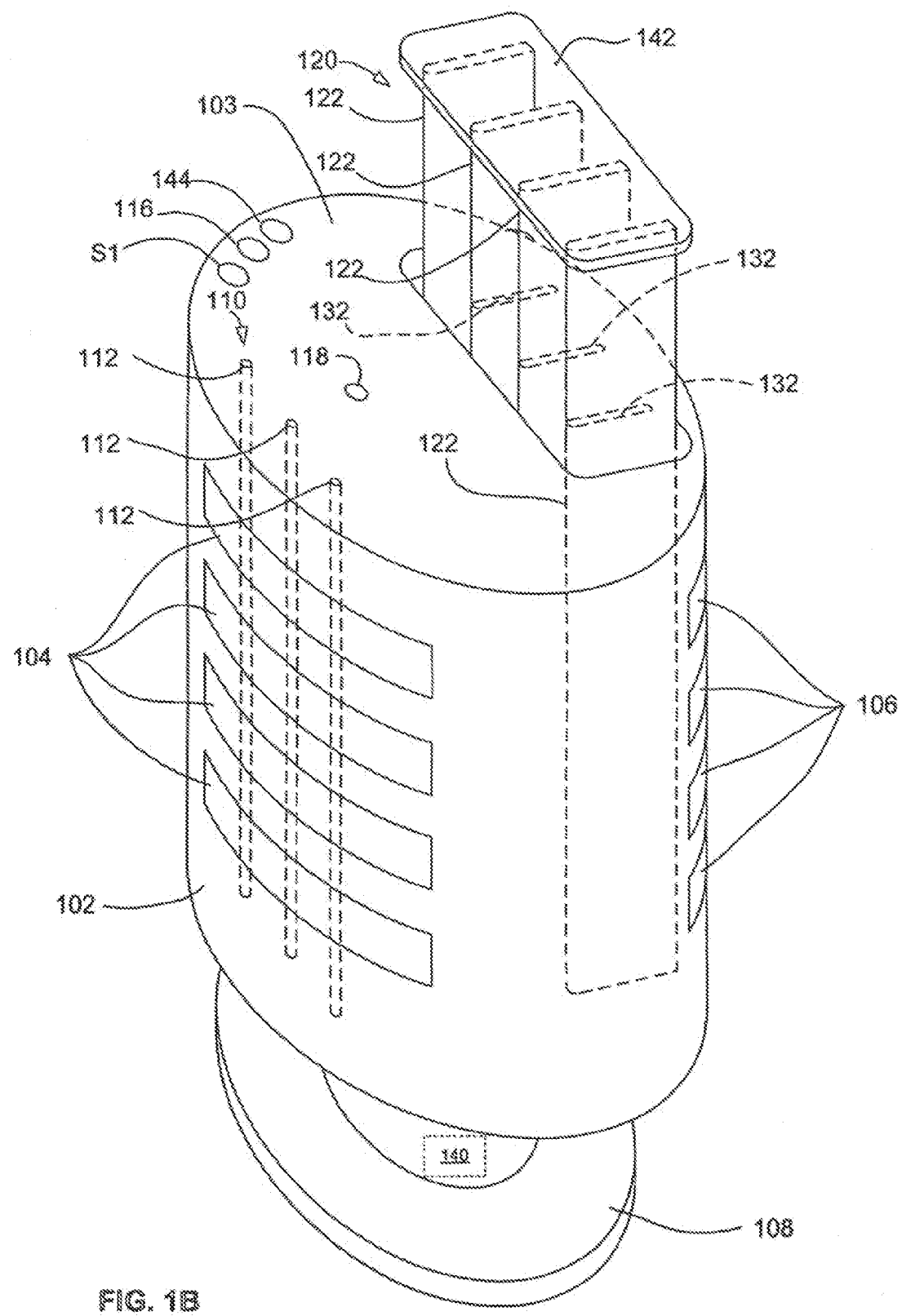

As shown in FIG. 1B, the above described electrodes are likely within a housing 102. The exemplary housing 102 includes intake vents 104, outlet vents 106, and a base pedestal 108. Preferably, the housing 102 is free standing and/or upstandingly vertical and/or elongated. The base 108, which may be pivotally mounted to the remainder of the housing, allows the housing 102 to remain in a vertical position.

The electro-kinetic transporter and conditioner system is likely powered by an AC-DC power supply that is energizable or excitable using switch S1. Switch S1, along with the other user operated switches such as a control dial 144, are preferably located on or near a top 103 of the housing 102. Additional, a boost button 116, as well as one or more indicator lights 118, can be located on the housing 102. The whole system is self-contained in that other than ambient air, nothing is required from beyond the housing 102, except perhaps an external operating voltage, for operation.

A user-liftable handle member 142 is shown as being affixed the collector array 120 of collector electrodes 122, which normally rests within the housing 102. The housing 102 also encloses the array 110 of emitter electrodes 112 and the array 130 of driver electrodes 132. In the embodiment shown, the handle member 142 can be used to lift the collector array 110 upward causing the collector electrodes 122 to telescope out of the top of the housing 102 and, if desired, out of the housing 102 for cleaning, while the emitter electrode array 110 and the driver electrodes array 130 remain within the housing 102. As is evident from FIG. 1B, the collector array 110 can be lifted vertically out from the top 103 of the housing along the longitudinal axis or direction of the elongated housing 102. This arrangement with the collector electrodes 122 removable through a top portion of the housing 102, makes it easy for a user to pull the collector electrodes 122 out for cleaning, and to return the collector electrodes 122, with the assistance of gravity, back to their resting position within the housing 102. If desired, the driver array 130 may be made similarly removable.

There need be no real distinction between vents 104 and 106, except their locations relative to the electrodes. These vents serve to ensure that an adequate flow of ambient air can be drawn into the housing 102 and made available to the electrodes, and that an adequate flow of ionized cleaned air moves out from housing 102.

During operation of system 100, the high voltage generator 140 produces a high voltage potential difference between the emitter electrodes 112 (of the emitter array 110) and the collector electrodes 122 (of the second array 120). For example, the voltage on the emitter electrodes 112 can be +6 KV, while the voltage on the collector electrodes 322 can be −10 KV, resulting in a 16 KV potential difference between the emitter electrodes 312 and collector electrodes 322. This potential difference will produces a high intensity electric field that is highly concentrated around the emitter electrodes 112. More specifically, a corona discharge takes place from the emitter electrodes 112 to the collector electrodes 122, producing charged ions. Particles (e.g., dust particles) in the vicinity of the emitter electrodes 112 are charged by the ions. The charged ions are repelled by the emitter electrodes 112, and are attracted to and deposited on the collector electrodes 122.

In embodiments that include driver electrodes 132 (which are preferably, but not necessarily insulated), further electric fields are produced between the driver electrodes 132 and the collector electrodes 122, which further push the particles toward the collector electrodes 122. Generally, the greater this electric field between the driver electrodes 132 and collector electrodes 122, the greater the particle collection efficiency.

The freestanding housing 102 can be placed in a room (e.g., near a corner of a room) to thereby clean the air in the room, circulate the air in the room, and increase the concentration of negative ions in the room. The number of electrodes shown in FIG. 1 is merely exemplary, and is not meant to be limiting. As mentioned above, a system 100 can include as few as one emitter electrode 112 and one collector electrode 122.

Other voltage arrangements are also likely, as explained in the '420 application, which was incorporated by reference above. For example, the emitter electrodes 112 can be grounded (rather than being connected to the positive output terminal of the high voltage generator 140), while the collector electrodes 122 are still negatively charged, and the driver electrodes 132 are still grounded. Alternatively, the driver electrodes 132 can be connected to the positive output terminal of the high voltage generator 140 (rather than being grounded), the collector electrodes 122 are negatively charged, and the emitter electrodes 112 are still grounded. In another arrangement, the emitter electrodes 112 and driver electrodes 132 can be grounded, while the collector electrodes 122 have a high negative voltage potential or a high positive voltage potential. It is also possible that the instead of grounding certain portions of the electrode arrangement, the entire arrangement can float (e.g., the driver electrodes 132 and the emitter electrodes 112 can be at a floating voltage potential, with the collector electrodes 122 offset from the floating voltage potential). Other voltage variations are also possible while still being within the spirit as scope of the present invention.

The emitter electrodes 112 are likely wire-shaped, and are likely manufactured from a wire or, if thicker than a typical wire, still has the general appearance of a wire or rod. While the collector electrodes are typically in need of cleaning more often then the emitter electrodes, the emitter electrodes can eventually accumulate a deposited layer or coating of fine ash-like material. Additionally, dendrites may grow on the emitter electrodes. If such deposits are allowed to accumulate, the collecting efficiency of the system will eventually be degraded. Further, such deposits may produce an audible oscillation that can be annoying to persons near the system. Embodiments of the present invention relate to new systems and methods for cleaning emitter electrodes.

Figure 2A:
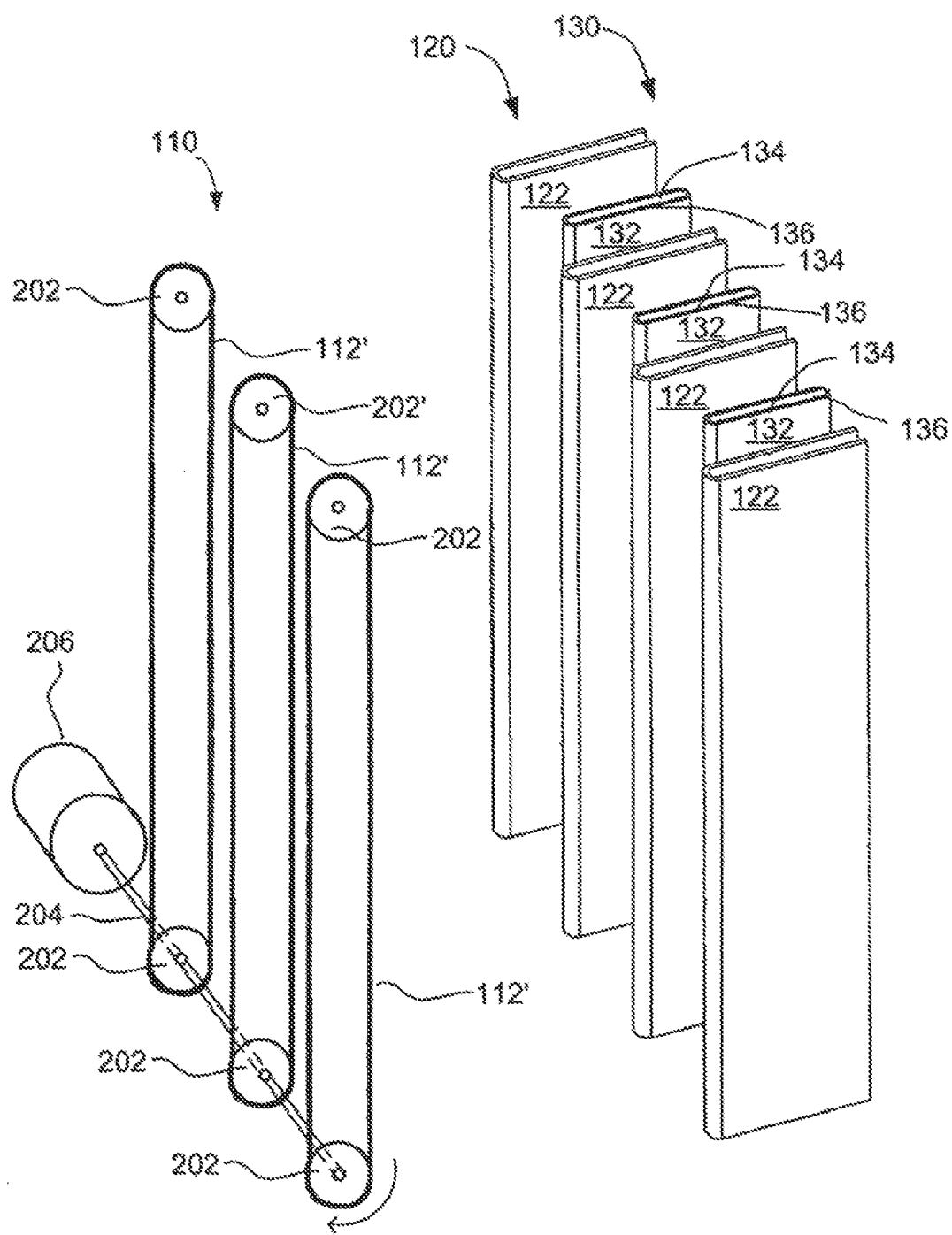
FIG. 2A illustrates an electro-kinetic conditioner system that includes wire loop emitter electrodes, in accordance with embodiments of the present invention.

FIG. 2A illustrates emitter electrodes 112' according to embodiments of the present invention. In these embodiments, each emitter electrode 112' is made from a loop of wire that is strung around a pair of rotatable wheels or pulleys 202. In the arrangement shown, the plane of the each wire loop is generally parallel with the flat downstream walls of the collector electrodes 122. With this arrangement, half of each wire loop 112' will be closer to the collector electrodes 122 that the other half of that loop.

In another embodiment (not shown), each wire loop 112' is in a common plane, which is generally perpendicular to the downstream flat walls of the collector electrodes 122. In such an embodiment, both halves of each wire loop 112' will be equally distant from the collector electrodes 122, allowing each half of the wire loop 112' to simultaneously act as an ion emitting surface. By making the diameter of each pulley equal to a desired distance between adjacent emitter electrodes, the two halves of each wire loop 112' will be the desired distance apart. It is also within the scope of the present invention that the wire loop emitter electrodes 112' are not parallel with the collector electrodes 122.

For each pair of pulleys 202, at least a portion of one of the pulleys 202 can be electrically connected to the positive or negative terminal of the voltage source 140 (or to ground), to thereby impart a desired voltage potential to the wire loop emitter electrode 112' strung around the pulleys 202.

Each wire loop emitter electrode 112' can be rotated by rotating one of the pair of pulleys 202 around which the wire 112' is strung. For example, rotation of the lower pulleys 202 (and/or upper pulleys 202) will cause the wire loop emitter electrodes 112' to rotate, allowing for frictional cleaning of the wire emitter electrodes 112', as will be described with reference to FIGS. 2B-2D. A common shaft 204 can connect all of the lower pulleys 202 (or upper pulleys), thereby allowing a single motor 206 or manual mechanism to rotate all of the wire loop emitter electrodes 112'. Alternatively, the pulleys can be connected through a gear system, or the like. Where a motor is used to rotate the pulleys, a button to activate the motor can be placed on the system housing 102. In other embodiments, the motor can be periodically activated, or activated in response to some event, such as detection of arcing, or detection of the system being turned on, etc. Alternatively, a crank, thumbwheel, or other manual mechanism can be placed on (or be accessible from) the system housing 102 and used to allow for manual rotation of the pulleys 202. In accordance with an embodiment of the present invention, an indicator (e.g., a light) can tell a user when they should use a manual mechanism to rotate, and thus clean, the wire emitter electrodes 112'.

Figure 2D:
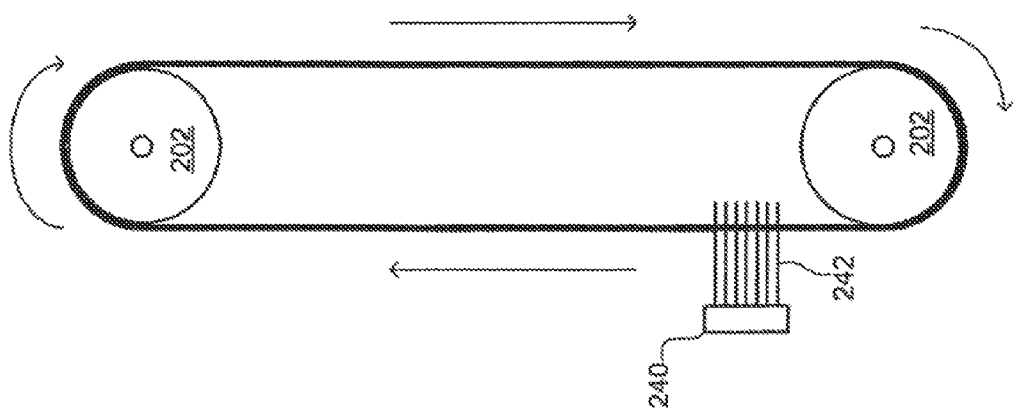
Figure 2C:
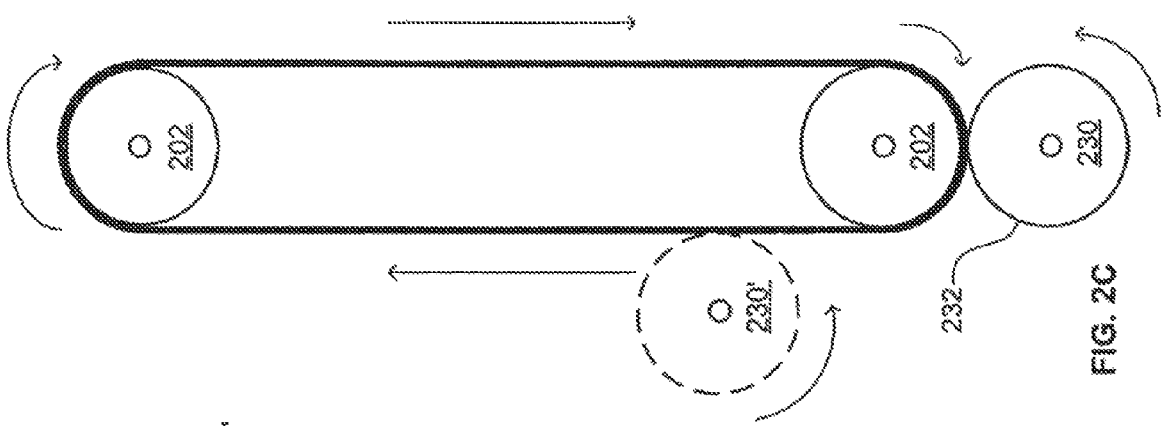
Figure 2B:
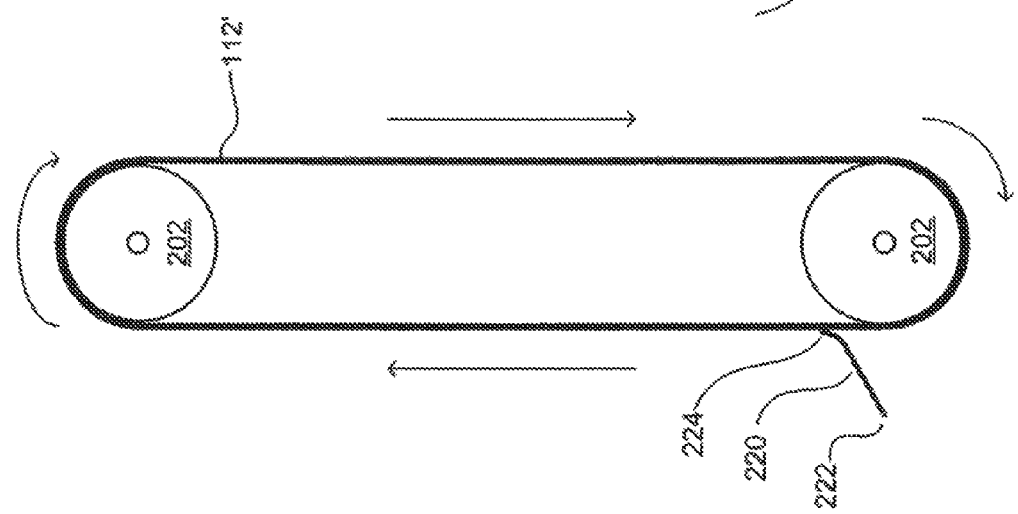

Referring now to FIG. 2B, a pair of pulleys 202 and a single wire loop emitter electrode 112' are shown. Also shown is a scraper 220, which is used to frictionally clean the emitter electrode 112' as it is rotated. In accordance with an embodiment of the present invention, the scraper 220 is made from a sheet or strip of flexible insulating material, such as those marketed under the trademarks MYLAR and KAPTON. The sheet of insulating material includes a first end 222 attached within the housing 102 and a free end 224 that scrapes against the emitter electrode 112' as it is rotated. This sheet 220 can be attached within the housing so that the sheet faces the emitter electrodes 112' and is nominally in a plane perpendicular the emitter electrode 112'. Such sheet material preferably has high voltage breakdown, high dielectric constant, can withstand high temperature, and is flexible. Although not required, a slit can be located (e.g., cut) in the free end 224 of the sheet such that wire electrode fits 112' into the slit.

Whenever one of the pulleys 202 is rotated, the wire loop emitter electrode 112' rotates and frictionally scrapes against the free end 224 of the scraper 220 (or the slit cut therein), causing debris to be frictionally removed from the wire loop emitter electrode 112', thereby cleaning the electrode 112'.

In accordance with another embodiment of the present invention, the scraper 220 is inflexible, and has a free end biased against the wire electrode 112', so that it scrapes against the wire electrode 112' as the wire electrode 112' rotates. As with the flexible embodiment, the inflexible scraper 220 may or may not include a slit within which with wire electrode fits 112'.

In embodiments including more than one wire loop emitter electrode 112', there can be a separate scraper 220 for each wire loop electrode 112'. Alternatively, a single scraper 220 can be made wide enough to clean more than one, and possible all, of the wire loop electrodes 112'. Such a scraper 220 may or may not include a slit that corresponds to each electrode 112' that it cleans.

Referring now to FIG. 2C, in accordance with another embodiment of the present invention, an additional rotatable pulley or wheel 230 is located adjacent one of the pulleys 202 about which the wire loop emitter electrode 112' rotates. An outer surface 232 of the wheel 230, referred to hereafter as a cleaning wheel, contacts a portion of the emitter electrode 112' as the electrode 112' is rotated about the pulleys 202. The outer surface 232 is preferably rough or bristled, so that the cleaning wheel 230 cleans debris from the electrode 112' as it comes in contact with the electrode 112'. Friction between the wire loop emitter electrode 112' and the outer surface 232 of the cleaning wheel 230 will cause the cleaning wheel 230 to rotate, when the wire loop emitter electrode 112' rotates. Accordingly, there is no need for a separate motor or other mechanism for rotating the cleaning wheel 230, although one can be included. It is also possible that the rotation of the cleaning wheel 230 could be used to cause one of the pulleys 202 to rotate, thereby causing the rotation of the wire loop emitter electrode 112'. It is also possible that gears, or the like, connect a pulley 202 and the cleaning wheel 230, so that they both are rotated by a common motor or manual mechanism. Preferably, the cleaning wheel 230 and adjacent pulley 202 rotate in opposite directions, as shown in FIG. 2C.

Alternatively, or additionally, a cleaning wheel 230' be placed at other locations adjacent the wire loop emitter electrode 112', as shown in phantom.

Referring now to FIG. 2D, in accordance with another embodiment of the present invention, a brush 240 is located adjacent to and in contact with the wire loop emitter electrode 112'. The brush 240 cleans debris from the emitter electrode 112' as it rotates past the brush 240. The brush 240 includes bristles 242 which extend at least as far as, and possibly past, an adjacent portion of the electrode 112'. The bristles 242 preferably have a high voltage breakdown, have a high dielectric constant, and can withstand high temperature. The brush 240 can be attached within the housing 102 so that the bristles 242 extend toward the emitter electrode 112'. In FIG. 2D, the brush 240 is shown as being located between the two pulleys 230. It is also possible that the brush 240 can be located adjacent one of the pulleys 202.

In embodiments including more than one wire loop emitter electrode 112', there can be a separate brush 240 for each wire loop electrode 112'. Alternatively, a single brush 240 can be made wide enough to clean more than one, and possible all, of the wire loop electrodes 112'.

It is to be understood that in the embodiments of FIGS. 1A, 1B, 2A, 2B, 2C and 2D, if desired, the portion of each wire loop 112' that is further from the collector electrodes 122 can be shielded from the portion of each wire loop 112' that is closest to the collector electrodes 122, so that the further portion of the wire loop 112' does not interfere with the portion of the wire loop 112' that is closest to the collector electrode 122. This can be accomplished, for example by including an insulating shield or wall between each pair of pulleys 202.

Referring now to FIG. 2E, in another embodiment of the present invention, a wire emitter electrode 112" is unwound from one pulley or spool 202 (e.g., the lower spool) and wound onto a second pulley or spool 202 (e.g., the upper spool). As with the above described embodiments, a motor, hand crank, thumb wheel, or any other mechanism for rotating the windup pulley 202 (e.g., the lower wheel) can be used. If a motor is used, the motor can be periodically activated, or activated in response to some event, such as detection of arcing, or detection of the system being turned on, detection of a button being pressed, etc. In this embodiment, rather than cleaning the wire emitter electrode 112", a debris covered portion of the wire 112" gets wound up, and an unused clean portion of the wire 112" gets unwound and exposed, to act as the emitter. Eventually, when the wire 112" is used up, a new spool or wheel 202 of wire 112" can be installed. This embodiment is somewhat analogous to a rotating cloth towel machine, which is commonly used in commercial restrooms.

In embodiments including more than one emitter electrode, there can be a separate spool 202 for each emitter electrode 112". Alternatively, a single spool can be made wide enough to contain multiple wound emitter electrodes 112", which are spread apart from one another along the wide spool.

FIGS. 3A-3E will now be used to describe how a spring loaded cleaning member 302, can be used to clean an emitter electrode 112. As shown in FIG. 3A, the member 302 will normally rest near the bottom of the emitter electrode 112, above a spring 306 (but not necessarily in direct contact with the spring 306, as can be appreciated from FIGS. 3D and 3E). The emitter electrode 112 passes through a channel 304 through the member 302. The member 302 is preferably fabricated from a material that can withstand high temperature and high voltage, and is not likely to char, e.g., ceramic, glass, or an appropriate plastic.

In response to the spring 306 being compacted or downwardly biased, as shown in FIG. 3B, the spring (when released) will cause the member 302 to move upward, and more specifically project upward, along the emitter electrode 112, as shown in FIG. 3C. Preferably, the force produced by the spring 306 is sufficient to cause the member 302 to project upward the entire length of the emitter electrode 112. Eventually, gravity will cause the member 302 to travel downward along the emitter electrode 112, where it will eventually come to rest near the bottom of the emitter electrode 112, where it started. The member 302 will frictionally remove debris from the emitter electrode 112 is it moves upward, and as it moves downward.

The member 302 need not be circular, and may instead have any other shape, such as cylindrical, bell shaped, square, oval, etc. While it may be easiest to form the channel 304 with a circular cross-section, the cross-section could in fact be non-circular, e.g., triangular, square, irregular shaped, etc. The channel 304 may be formed through the center of the member 302, or may be formed off-center to give asymmetry to the member 302. An off-centered member will have a mechanical moment and will tend to slightly tension the emitter electrode 112 as the member slides up and down, and can improve cleaning characteristics. It is also possible that the channel be slightly inclined, to impart a different frictional cleaning action.

The spring 306 can be compressed (i.e., loaded) in various manners. In accordance with an embodiment of the present invention, a plunger-like mechanism 310 is used to compress the spring 306, similar to how a plunger compresses a spring in a pin-ball machine. The plunger-like mechanism 310 can be manually pulled downward. As shown in FIG. 3E, in other embodiments, the plunger 310 can be part of, or controlled by, an electromagnetic solenoid or a piezoelectric actuator mechanism 312, which can be used to pull the plunger-like mechanism downward. When the plunger 310 is released, manually, or electrically, the spring 306 will cause the member 302 to project upward along the emitter electrode 112, as explained above. Other ways of controlling the plunger 310 are also within the spirit and scope of the present invention.

Where a solenoid or actuator mechanism 312 is used, a button to activate the mechanism can be placed on the system housing (e.g., 102). In another embodiment, the solenoid or actuator 312 can be activated periodically, or activated in response to some event, such as detection of arcing, or detection of the system being turned on, etc. In accordance with an embodiment of the present invention, an indicator (e.g., a light) can tell a user when they should manually pull the plunger 310, which can be arranged in such a manner that it is accessible from outside the housing 102.

In embodiments including more than one emitter electrode 112, there can be a separate cleaning member 302 and spring 306 for each emitter electrode 112. There can also be a separate plunger 310, and even a separate electromagnetic solenoid or piezoelectric actuator mechanism 312, for each cleaning member 304. Alternatively, a plurality of plungers 310 can be linked together and controlled by a single electromagnetic solenoid or piezoelectric actuator mechanism 312. It is even possible that a wide cleaning member 302 can include multiple channels 304, and thus be used to clean more than one, and possible all, of the emitter electrodes 112.

In another embodiment, described with reference to FIGS. 4A and 4B, a lever 402 pivots about a fulcrum 404. A first end 406 of the lever 402 can extend outside the housing 102 (e.g., through an opening in the housing 102) so that it is accessible to a user. A second end 408 of the lever 402 rests under the cleaning member 302. As shown in FIG. 4B, when a downward force is applied to the first end 406 of the lever 402 (e.g., due to a user pushing down with their finger), the second end 408 pivots upward, causing the member 302 to project upward (and eventually fall downward), thereby frictionally cleaning debris from the emitter electrode 112.

Referring to FIG. 4C, which is a top view of an exemplary lever 402, the second end 408 likely includes a slit 410, so that the second end 408 can straddle the emitter electrode 112 and be under the member 302 when it is at rest. The lever 402 and fulcrum 404 can be arranged and/or weighted such that the second end 408 falls downward when the user stops pushing down on the first end 404. Alternatively, or additionally, the member 302 will cause the second end 408 to move downward when the member 302 travels back down the emitter electrode 112 due to gravity.

In embodiments including more than one emitter electrode 112, there can be a separate lever 402 for each electrode 112. The first ends 404 of the multiple levers 402 can be connected together so that a user need only push down one lever to clean multiple emitter electrodes 112. Alternatively, the second end 408 of a single lever 402 can be made wide enough such that when it pivots upward, it forces multiple cleaning members 302 upward, and thus, a single lever 402 can be used to clean multiple emitter electrodes 112. In such an embodiment, the second end 408 likely includes a slit 410 for each emitter electrode 112 that it is used to clean, as shown FIG. 4D, which is the top view of a level 402 according to an alternative embodiment of the present invention. This enables the second end 408 to straddle multiple emitter electrodes 112 and be under multiple cleaning members 302 when they are at rest. It is also possible that a single lever 402 can be used to force a single cleaning member 302 upward, where the single member 302 is a wide cleaning member that includes multiple channels 304, to thereby clean multiple, and possible all, of the emitter electrodes 112.

The lever 402 can be controlled by an electromagnetic solenoid or a piezoelectric actuator mechanism, similar to the mechanism 312 discussed above with reference to FIG. 3E. Other ways of, and mechanisms for, controlling the lever 402 are also within the spirit and scope of the present invention.

Where a solenoid or actuator mechanism is used, a button to activate the mechanism can be placed on the system housing (e.g., 102). In another embodiment, the solenoid or actuator can be activated periodically, or activated in response to some event, such as detection of arcing, or detection of the system being turned on, etc. In accordance with an embodiment of the present invention, an indicator (e.g., a light) can tell a user when they should manually use the lever 402 to clean the emitter electrode(s) 112.

In another embodiment, described with reference to FIGS. 5A-5C, a plucker 502 is used to pluck an emitter electrode 112, to thereby vibrate the emitter electrode 112, causing debris to fall off the emitter electrode. The plucker 502 includes a first end 506, which can extend outside the housing 102 (e.g., through an opening in the housing 102) so that it is accessible to a user. A second end 508 of the plucker 502 includes a lip 510 or similar structure that can be used to engage the emitter electrode 112. The plucker 502 can rest in a channel 512 or be supported by another structure. As shown in FIG. 5B, the plucker 502 can be moved toward the emitter electrode 112, such that the lip 510 engages the emitter electrode 112. When the plucker 502 is then pulled away from the emitter electrode 112, the emitter electrode 112 will vibrate, as exaggeratedly shown in FIG. 5C. Such vibration will cause at least a portion of the debris that accumulates on the emitter electrode 112 to shake free.

In an alternative embodiment, rather than having a plucker 502 that moves toward and away from the emitter electrode 112, a plucker can rotate in a plane that is generally perpendicular to the emitter 112. A lip or similar structure can engage the emitter electrode 112 when the plucker is rotated toward the emitter electrode 112. Then, when the plucker is rotated away from the emitter electrode 112, the emitter electrode 112 will vibrate, thereby causing at least a portion of the debris that accumulates on the emitter electrode 112 to shake free. In still another embodiment, a plucker can pluck the emitter electrode 112 when it is rotated toward and past the emitter electrode 112.

In embodiments including more than one emitter electrode 112, there can be a separate plucker 502 for each electrode 112. Alternatively, a single plucker can be made to pluck multiple emitter electrodes at once.

As mentioned above, the first end 506 of the plucker 502 can extend outside the housing 102, thereby enabling a user to manually operate the plucker 502. Alternatively, the plucker 502 can be controlled by, an electromagnetic solenoid or a piezoelectric actuator mechanism, similar to the mechanism 312 discussed above with reference to FIG. 3E. Other ways of, and mechanisms for, controlling the plucker 502 are also within the spirit and scope of the present invention.

Where a solenoid or actuator mechanism is used, a button to activate the mechanism can be placed on the system housing (e.g., 102). In another embodiment, the solenoid or actuator can be activated periodically, or activated in response to some event, such as detection of arcing, or detection of the system being turned on, etc. In accordance with an embodiment of the present invention, an indicator (e.g., a light) can tell a user when they should manually use the plucker 502 to clean the emitter electrode(s) 112.

Figure 6B:
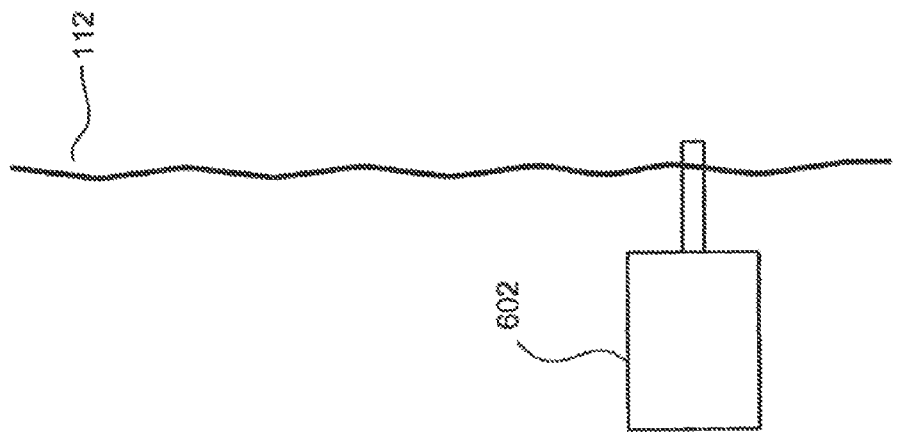
FIGS. 6A and 6B illustrate embodiments of the present invention where a vibrating unit is used to vibrate an emitter electrode.
Figure 6A:
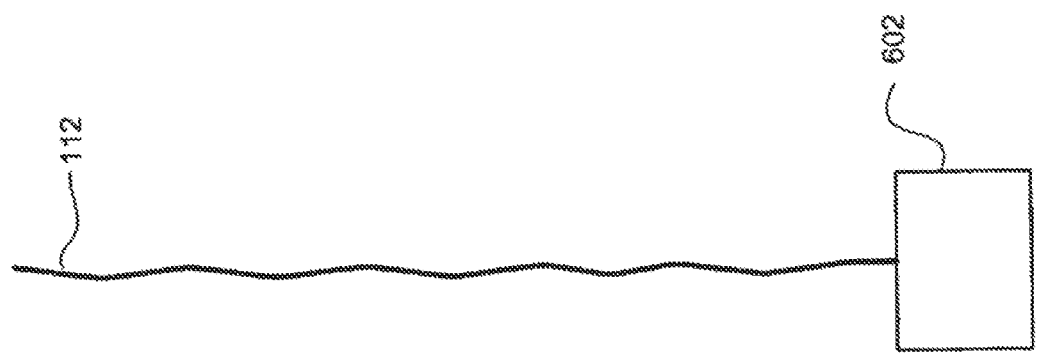

There are other schemes for vibrating an emitter electrode 112, to cause debris to shake free from the emitter electrode 112. For example, a vibrating unit 602 can be connected to one end of the emitter electrode 112, as shown in FIG. 6A. Alternatively, the vibrating unit 602 can be connected somewhere along the length of the emitter electrode, as shown in FIG. 6B. The vibrating unit 602 can include a piezoelectric vibrator. In another example, the vibrating unit 602 can include a simple DC motor with an eccentric weight connected to the rotor shaft of the DC motor. In another embodiment, the rotor of the DC motor is eccentric, to thereby produce vibration. Alternatively, the vibrating unit 602 can use electro-magnetics to produce vibration. In another example, the vibrating unit 602 includes a vibratory gyroscope. These are just a few examples of how the vibrating unit 602 can vibrate the emitter electrode 112. Other mechanisms for vibrating the emitter electrode 112 are also within the spirit and scope of the present invention.

In embodiments including more than one emitter electrode 112, there can be a separate vibrating unit 602 for each emitter electrode 112. Alternatively, a single vibrating unit 602 can be used to vibrate multiple, and possible all, of the emitter electrodes 112.

A button to activate the vibrating unit 602 can be placed on the system housing (e.g., 102). In another embodiment, the vibrating unit 602 can be activated periodically, or activated in response to some event, such as detection of arcing, or detection of the system being turned on, etc. In accordance with an embodiment of the present invention, an indicator (e.g., a light) can tell a user when they should press the button that will activate the vibrating unit 602.

Figure 7:
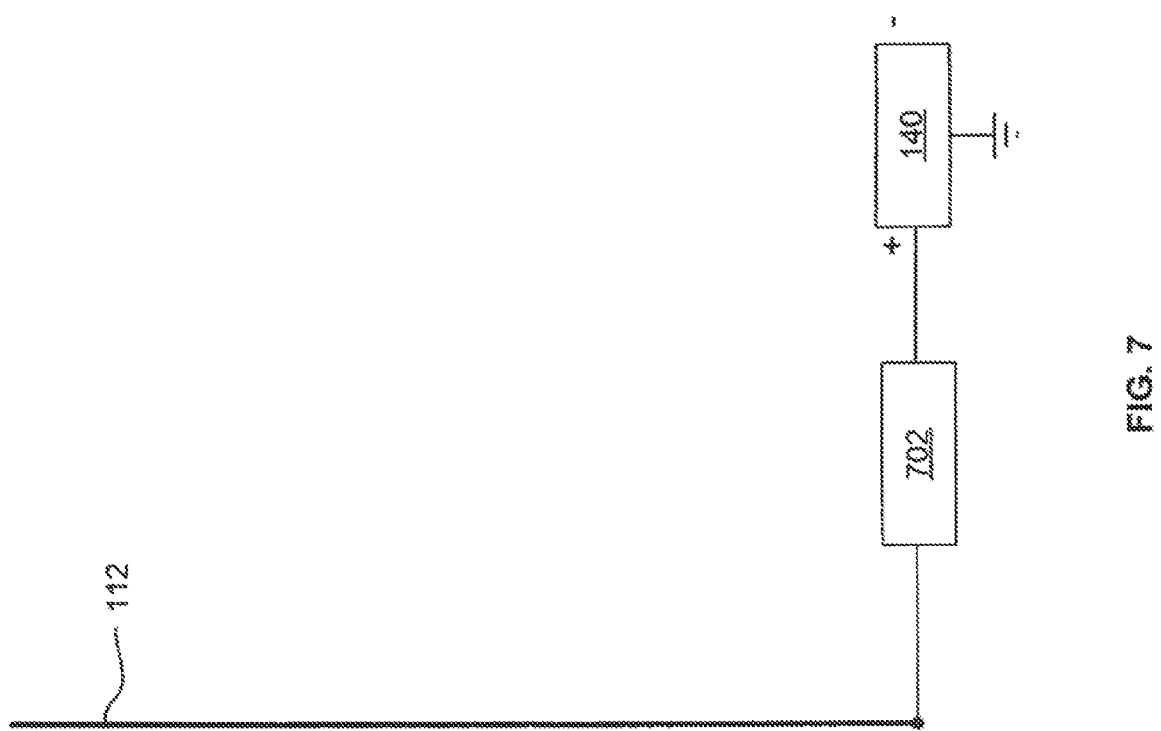
FIG. 7 illustrates embodiments of the present invention where a current control circuit is used to heat an emitter electrode.

In another embodiment, a sufficient current is applied to an emitter electrode 112 so as to heat the emitter electrode 112 to a sufficient temperature to cause debris collected on the emitter electrode to be burned off. This can be accomplished, e.g., by connecting a current control circuit 702 between the voltage source 140 and the emitter electrode 112, as shown in FIG. 7. Using simple transistors and/or resistors, the current control circuit 702 can provide one current/voltage to the emitter electrode(s) 112 when the emitter electrode(s) 112 is being used to charged particles, in the manner discussed above with reference to FIG. 1A. The current control circuit 702 can provide a different current/voltage (likely, a significantly higher current) to heat up the emitter electrode(s) 112, thereby cleaning the emitter electrode(s) 112.

A button to initiate electrode heating can be placed on the system housing 102. In another embodiment, the current control unit 702 can be instructed to cause the heating of the emitter electrode(s) 112 periodically, or in response to some event, such as detection of arcing, or detection of the system being turned on, etc. In accordance with an embodiment of the present invention, an indicator (e.g., a light) can tell a user when they should press the button that will initiate the heating of the emitter electrode(s) 112.

Figure 8:
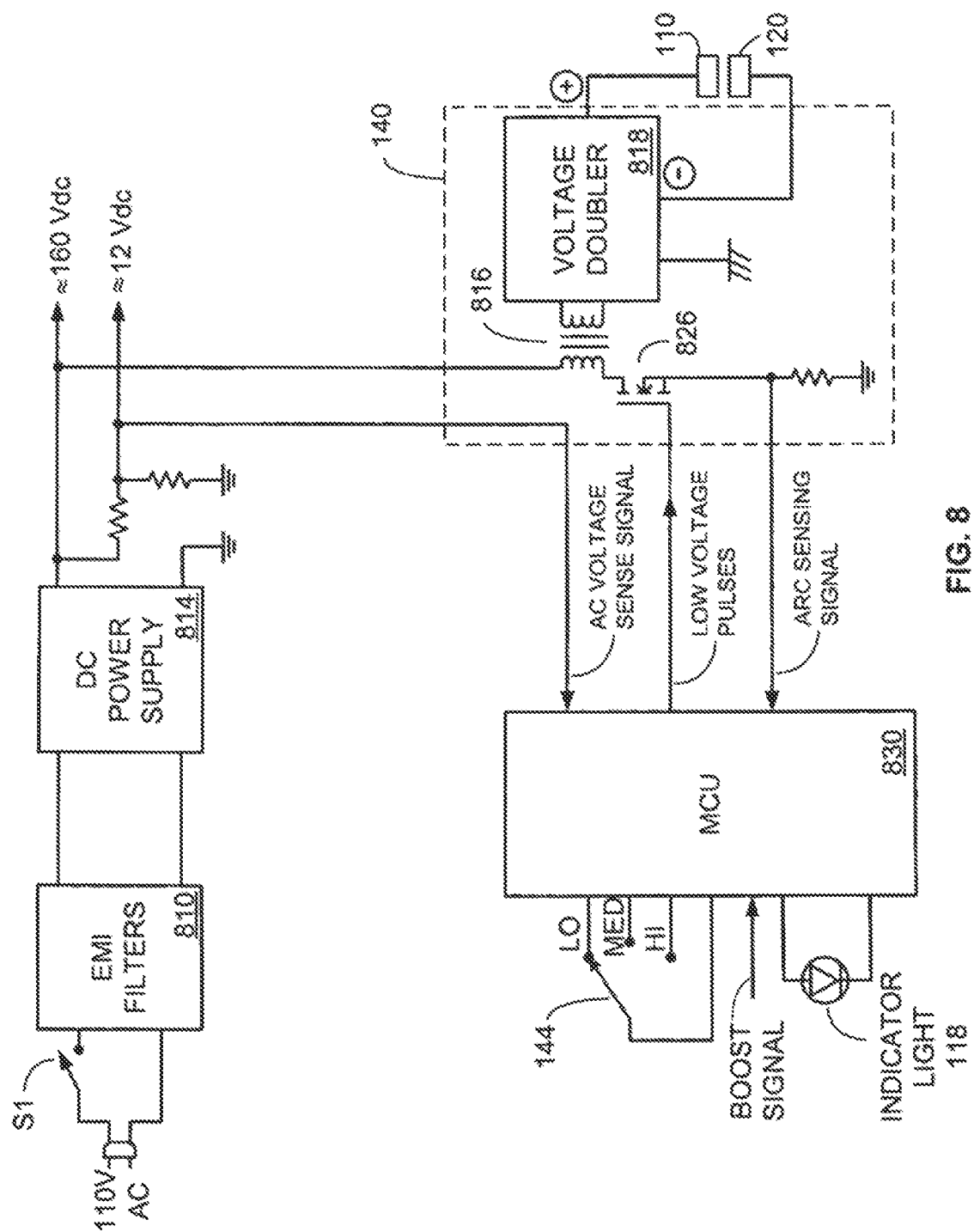
FIG. 8 is a block diagram of an exemplary circuit used to the drive and control an electro-kinetic conditioner system, according to embodiments of the present invention.

FIG. 8 illustrates an electrical block diagram for driving the electro-kinetic systems described above, according to embodiments of the present invention. An electrical power cord that plugs into a common electrical wall socket provides a nominal 110 VAC. An electromagnetic interference (EMI) filter 810 is placed across the incoming nominal 110 VAC line to reduce and/or eliminate high frequencies generated by the various circuits. Batteries can alternatively be used to power systems, as would be clear to one of ordinary skill in the art.

A DC Power Supply 814 is designed to receive the incoming nominal 110 VAC and to output a first DC voltage (e.g., 160 VDC) for the high voltage generator 140. The first DC voltage (e.g., 160 VDC) is also stepped down through a resistor network to a second DC voltage (e.g., about 12 VDC) that a micro-controller unit (MCU) 830 can monitor without being damaged. The MCU 830 can be, for example, a Motorola 68HC908 series micro-controller, available from Motorola. In accordance with an embodiment of the present invention, the MCU 830 monitors the stepped down voltage (e.g., about 12 VDC), which is labeled the AC voltage sense signal in FIG. 8, to determine if the AC line voltage is above or below the nominal 110 VAC, and to sense changes in the AC line voltage. For example, if a nominal 110 VAC increases by 10% to 121 VAC, then the stepped down DC voltage will also increase by 10%. The MCU 830 can sense this increase and then reduce the pulse width, duty cycle and/or frequency of the low voltage pulses to maintain the output power (provided to the high voltage generator 140) to be the same as when the line voltage is at 110 VAC. Conversely, when the line voltage drops, the MCU 830 can sense this decrease and appropriately increase the pulse width, duty cycle and/or frequency of the low voltage pulses to maintain a constant output power. Such voltage adjustment features of the present invention also enable the same unit to be used in different countries that have different nominal voltages than in the United States (e.g., in Japan the nominal AC voltage is 100 VAC).

The high voltage pulse generator 140 is coupled between the first electrode array 110 and the second electrode array 120, to provide a potential difference between the arrays. Each array can include one or more electrodes. The high voltage generator 140 may additionally, or alternatively, apply a voltage potential to the driver electrode array 130. The high voltage pulse generator 140 may be implemented in many ways. In the embodiment shown, the high voltage pulse generator 140 includes an electronic switch 826, a step-up transformer 816 and a voltage multiplier 818. The primary side of the step-up transformer 816 receives the first DC voltage (e.g., 160 VDC) from the DC power supply. An electronic switch receives low voltage pulses (of perhaps 20-25 KHz frequency) from the micro-controller unit (MCU) 830. Such a switch is shown as an insulated gate bipolar transistor (IGBT) 826. The IGBT 826, or other appropriate switch, couples the low voltage pulses from the MCU 830 to the input winding of the step-up transformer 816. The secondary winding of the transformer 816 is coupled to the voltage multiplier 818, which outputs high voltages to the emitter and collector electrode arrays 110 and 120. In general, the IGBT 826 operates as an electronic on/off switch. Such a transistor is well known in the art and does not require a further description.

When driven, the generator 140 receives the low input DC voltage (e.g., 160 VDC) from the DC power supply 814 and the low voltage pulses from the MCU 830, and generates high voltage pulses of preferably at least 5 KV peak-to-peak with a repetition rate of about 20 to 25 KHz. Preferably, the voltage multiplier 818 outputs about 6 to 9 KV to the emitter array 110, and about 12 to 18 KV to the collector array 120. It is within the scope of the present invention for the voltage multiplier 818 to produce greater or smaller voltages. The high voltage pulses preferably have a duty cycle of about 10%-15%, but may have other duty cycles, including a 100% duty cycle.

The MCU 830 receives an indication of whether the control dial 144 is set to the LOW, MEDIUM or HIGH airflow setting. The MCU 830 controls the pulse width, duty cycle and/or frequency of the low voltage pulse signal provided to switch 826, to thereby control the airflow output, based on the setting of the control dial 114. To increase the airflow output, the MCU 830 can increase the pulse width, frequency and/or duty cycle. Conversely, to decrease the airflow output rate, the MCU 830 can reduce the pulse width, frequency and/or duty cycle. In accordance with an embodiment, the low voltage pulse signal (provided from the MCU 830 to the high voltage generator 140) can have a fixed pulse width, frequency and duty cycle for the LOW setting, another fixed pulse width, frequency and duty cycle for the MEDIUM setting, and a further fixed pulse width, frequency and duty cycle for the HIGH setting.

The MCU 830 can provide various timing and maintenance features. For example, the MCU 830 can provide a cleaning reminder feature (e.g., a 2 week timing feature) that provides a reminder to clean the emitter electrodes 112 and/or collector electrode 122 (e.g., by causing indicator light 118 to turn on amber, and/or by triggering an audible alarm (not shown) that produces a buzzing or beeping noise). The MCU 830 can also provide arc sensing, suppression and indicator features, as well as the ability to shut down the high voltage generator 140 in the case of continued arcing. The MCU 830 can also initiate the cleaning of the emitter electrode(s) (112, 112', 112"), periodically, in response to arcing being detected, in response to a button being pressed by a user, etc. For example, referring back to the embodiments of 2A-2D, the MCU 830 can control the rotation of wire loop emitter electrode 112', e.g., by controlling one or more motors that rotate one or more pulleys 202. Referring back to FIG. 2E, the MCU 830 can similarly control the winding and unwinding of emitter electrode 112". Referring back to FIGS. 3A-3E, the MCU 830 can control the electro-mechanical mechanism 312 used to control the plunger 306. The MCU 830 may even control an electro-mechanical mechanism that appropriately maneuvers the lever 402, of FIGS. 4A-4D, or the plucker 502 of FIGS. 5A-5C. In another embodiment, the MCU 830 controls the vibrating unit 602 discussed with reference to FIGS. 6A and 6B. The MCU 830 may also control the heating of emitter electrodes 112, e.g., by controlling the current control unit 702, discussed above with reference to FIG. 7.

The MCU 830 can detect arcing in various manners. For example, an arc sensing signal can be provided to the MCU 830, as shown in FIG. 8. The arc sensing signal can be compared to an arcing threshold, to determine when arcing occurs. An arcing threshold may exist for each of the various setting of the control dial 144. For example, there can be a high threshold, a medium threshold and a low threshold. These thresholds can be current thresholds, but it is possible that other thresholds, such as voltage thresholds, can be used.

The arc sensing signal can be periodically sampled (e.g., one every 10 msec) to produce a running average current value. The MCU 830 can perform this by sampling the current at the emitter of the IGBT 826 of the high voltage generator 140 (see FIG. 8). The running average current value can be determined by averaging a sampled value with a previous number of samples (e.g., with the previous three samples). A benefit of using averages, rather than individual values, is that averaging has the effect of filtering out and thereby reducing false arcing detections. However, in alternative embodiments no averaging is used. The average current value can be compared to the appropriate threshold value. If the average current value does not equal or exceed the threshold value, then it is determined that arcing is not occurring. If the average current value is equal to or exceeds the threshold value, then it is determined that arcing is occurring, and the MCU 830 can attempt to stop the arcing by cleaning the emitter electrode using one of the embodiments discussed above.

Alternatively, the MCU 830 may simply turn on an indicator (e.g., indicator light 118) to inform a user that the emitter electrode(s) and collector electrode(s) should be cleaned. The user can then use one of the above described embodiments to clean the emitter electrodes. The collector electrodes are most likely cleaned by manually removing them from the housing, as was discussed above with respect to FIG. 1B. More detailed and alternative algorithms for detecting arcing are provided in commonly assigned U.S. patent application Ser. No. 10/625,401, entitled "Electro-Kinetic Air Transporter and Conditioner Devices with Enhanced Arcing Detection and Suppression Features," filed Jul. 23, 2003, which is incorporated herein by reference. Other schemes for detecting arcing are also within the spirit and scope of the present invention.

Many of the above described features of the present invention relate to cleaning emitter electrodes of electro-kinetic air transporter and conditioner devices. However, these features can also be used to clean wire-like emitter electrodes in electrostatic precipitator (ESP) devices that do not electro-kinetically transport air. ESP devices are similar to electro-kinetic air transporter and conditioner devices in that both types of devices electronically condition the air using emitter electrodes, collector electrodes, and possibly driver electrodes. However, ESP devices often rely on a mechanical means for moving air, such as a fan, rather than on electro-kinetic air movement. Nevertheless, debris may similarly accumulate on the emitter electrodes of ESP devices, thereby degrading the efficiency of the ESP system, and possibly producing annoying audible oscillations. Accordingly, the above described emitter cleaning features of the present invention can also be applied to ESP devices. Collectively, electro-kinetic air transporter and conditioner devices and ESP devices will be referred to hereafter simply as air conditioning devices, since both types of devices condition the air by electronically cleaning the air and producing ions.

The foregoing descriptions of the preferred embodiments of the present invention have been provided for the purposes of illustration and description. It is not intended to be exhaustive or to limit the invention to the precise forms disclosed. Many modifications and variations will be apparent to the practitioner skilled in the art. Modifications and variations may be made to the disclosed embodiments without departing from the subject and spirit of the invention as defined by the following claims. Embodiments were chosen and described in order to best describe the principles of the invention and its practical application, thereby enabling others skilled in the art to understand the invention, the various embodiments and with various modifications that are suited to the particular use contemplated. It is intended that the scope of the invention be defined by the following claims and their equivalents.

What is claimed:

1. A method of cleaning a flexible, elongate emitter electrode, the method comprising:
energizing the flexible, elongate emitter electrode strung at least partially around a rotor to establish a corona discharge to thereby motivate airflow;
rotating the rotor and thereby transiting a portion of the emitter electrode past one or more cleaning surfaces; and
frictionally engaging the cleaning surfaces and the transited portion of the emitter electrode and thereby removing debris therefrom.

2. The method of claim 1, wherein the rotor includes one or more of a pulley, a supply spool, a takeup spool and a wheel.

3. The method of claim 1,
wherein the cleaning surfaces include one or more of a scraper, a brush and a cleaning wheel.

4. The method of claim 1, wherein the elongate emitter electrode comprises a corona wire.

5. The method of claim 1,
wherein the elongate emitter electrode forms a continuous loop around the rotor and at least one other rotor.

6. The method of claim 1, further comprising:
at least one of unwinding a portion of the emitter electrode from a supply spool and winding a portion of the emitter electrode on a takeup spool.

7. The method of claim 1, further comprising:
alternately winding and unwinding a portion of the emitter electrode onto and from a spool.

8. The method of claim 1, wherein the transiting is performed continuously, periodically or responsive to an event.

9. The method of claim 1, further comprising:
energizing the elongate emitter electrode using a high voltage power supply, establishing a corona discharge from the elongate emitter electrode and thereby motivating flow of a fluid.

10. The method of claim 1, further comprising:
energizing the elongate emitter electrode using a high voltage power supply, establishing a corona discharge from the elongate emitter electrode and thereby precipitating particulate from a fluid.

11. The method of claim 1, further comprising:
coupling a supply voltage from a high voltage power supply to the emitter electrode via one or both of the rotor and another rotor.

12. The method of claim 1, further comprising frictionally engaging the cleaning surfaces and the transited portion of the emitter electrode along the perimeter of the rotor.

13. A method of making a corona discharge product, the method comprising: stringing an elongate emitter electrode at least partially about a rotor, the rotor moveable to transit the elongate emitter electrode;
positioning a cleaning surface in frictional engagement with the elongate emitter electrode, whereby debris may be frictionally removed from the elongate emitter electrode via movement of the rotor; and
providing an electrical path to the elongate emitter electrode by which the elongate emitter electrode may be energized to establish a corona discharge to thereby motivate airflow.

14. The method of claim 13, further comprising positioning a collector electrode sufficiently proximate to the elongate emitter electrode to establish a corona discharge between the emitter and the collector electrode.

15. The method of claim 13, further comprising coupling the emitter electrode to a power supply terminal.

16. A corona discharge device comprising:
a flexible, elongate emitter electrode energizable to establish a corona discharge to thereby motivate airflow;
a rotor about which the elongate emitter electrode is at least partially strung; and a cleaning surface in frictional engagement with the elongate emitter electrode;
wherein the rotor is movable to transit a portion of the elongate emitter electrode past the cleaning surface.

17. The corona discharge device of claim 16, wherein the emitter electrode is electrically coupled to a high voltage power supply to produce a corona discharge to thereby motivate flow of a fluid.

18. The corona discharge device of claim 16, wherein the emitter electrode is electrically coupled to a high voltage power supply to produce a corona discharge to thereby precipitate particles entrained in a fluid.

19. The corona discharge device of claim 16, further comprising:
a collector electrode and wherein the elongate emitter electrode is substantially parallel to an at least partially downstream wall of the collector electrode.

20. The corona discharge device of claim 16, further comprising:
a second elongate emitter electrode and second rotor, wherein the first and second elongate emitter electrodes form loops respectively about the rotor and the second rotor, the loops laying substantially in a common plane.

21. The corona discharge device of claim 20, further comprising:
a collector electrode having a substantially flat wall and wherein the common plane of the first and second elongate emitter electrode loops is generally perpendicular to the flat wall of the collector electrode.

22. The corona discharge device of claim 16, further comprising:
a collector electrode and wherein the elongate emitter electrode forms a continuous loop about the rotor and a second rotor; and
wherein two laterally adjacent loop segments are positioned substantially equidistant from the collector electrode.

23. The corona discharge device of claim 16, further comprising an insulating shield between two laterally adjacent segments of the elongate emitter electrode strung about the rotor.

24. The corona discharge device of claim 16, further comprising a second rotor, the rotor and second rotor comprising spools cooperative to alternately supply and take up the elongate emitter electrode.

25. A corona discharge apparatus comprising:
a flexible, elongate emitter electrode energizable to establish a corona discharge to thereby motivate airflow;
means for frictionally contacting the elongate emitter electrode; and
rotary means for transiting the elongate emitter electrode against the frictional contact means to thereby remove debris from the elongate emitter electrode.

26. The corona discharge apparatus of claim 25, further comprising: a high voltage power supply electrically coupled to the elongate emitter electrode via one of the rotary means and another rotary means.

27. An electro-kinetic air transport system comprising:
a flexible, elongate emitter electrode energizable to establish a corona discharge to thereby motivate airflow;
a voltage generator electrically coupled to the elongate emitter electrode;
a controller coupled to the voltage generator and configured to control a voltage output from the voltage generator;
a first rotor about which the elongate emitter electrode is at least partially strung, the rotor being moveable to transit the elongate emitter electrode; and
a cleaning surface positioned to frictionally engage the elongate emitter electrode and thereby clean the elongate emitter electrode during transiting of the elongate emitter electrode.

28. The electro-kinetic air transport system of claim 27, wherein the high voltage power supply is electrically coupled to the elongate emitter electrode via one of the rotor and another rotor.

29. The electro-kinetic air transport system of claim 27, wherein the controller is further configured to trigger at least one of a cleaning cycle, a cleaning reminder, rotation of the first pulley, and a shutdown cycle.

30. The electro-kinetic air transport system of claim 27, wherein the controller is configured to detect arcing by comparison of a running average current value and a threshold current value.

* * * * *